US011997910B2

(12) United States Patent
Nakagawa et al.

(10) Patent No.: US 11,997,910 B2
(45) Date of Patent: May 28, 2024

(54) SENSOR DEVICE AND SEMICONDUCTOR DEVICE

(71) Applicant: Semiconductor Energy Laboratory Co., Ltd., Atsugi (JP)

(72) Inventors: Takashi Nakagawa, Sagamihara (JP); Takayuki Ikeda, Atsugi (JP); Takahiro Fukutome, Atsugi (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 487 days.

(21) Appl. No.: 17/281,596

(22) PCT Filed: Oct. 2, 2019

(86) PCT No.: PCT/IB2019/058363
§ 371 (c)(1),
(2) Date: Mar. 31, 2021

(87) PCT Pub. No.: WO2020/075009
PCT Pub. Date: Apr. 16, 2020

(65) Prior Publication Data
US 2021/0391388 A1    Dec. 16, 2021

(30) Foreign Application Priority Data

Oct. 11, 2018 (JP) .................... 2018-192511

(51) Int. Cl.
*H10K 65/00* (2023.01)
*H10K 19/20* (2023.01)
*H10K 77/10* (2023.01)

(52) U.S. Cl.
CPC ............ *H10K 65/00* (2023.02); *H10K 19/20* (2023.02); *H10K 77/111* (2023.02)

(58) Field of Classification Search
CPC ...... H10K 65/00; H10K 19/20; H10K 77/111; H10K 59/12; H10K 2102/311;
(Continued)

(56) References Cited

U.S. PATENT DOCUMENTS 7,482,182 B2   1/2009   Yamazaki et al.
7,786,496 B2   8/2010   Yamazaki et al.
(Continued)

FOREIGN PATENT DOCUMENTS

CN    001453883 A    11/2003
CN    103022072 A    4/2013
(Continued)

OTHER PUBLICATIONS

International Search Report (Application No. PCT/IB2019/058363) dated Dec. 10, 2019.
(Continued)

*Primary Examiner* — Hung H Lam
(74) *Attorney, Agent, or Firm* — Eric J. Robinson; Robinson Intellectual Property Law Office, P.C.

(57) ABSTRACT

A flexible semiconductor device including a light-emitting element and a sensor element is provided. The semiconductor device includes a sensor device, a processor, and a communication device. The sensor device includes a first pixel and a second pixel formed over a flexible substrate. The first pixel includes a light-emitting element and a first transistor. The second pixel includes a sensor element having a photoelectric conversion function and a second transistor. Light emitted from the light-emitting element has a peak wavelength. A range of wavelength sensed by the sensor element includes the peak wavelength. A semiconductor layer of the first transistor and a semiconductor layer of the second transistor include the same element. A pixel electrode of the light-emitting element has a function of (Continued)

being electrically connected to the first transistor and a function of blocking diffusion light to the sensor element.

13 Claims, 17 Drawing Sheets

(58) Field of Classification Search
CPC ...... H10K 59/60; H10K 50/00; H10K 50/865; H10K 59/65; A61B 5/1455; G01J 1/02; G01N 21/27; H01L 27/146; H01L 27/15; H01L 29/786; H01L 31/12; H04N 25/70; H05B 33/02; H05B 33/14
See application file for complete search history.

(56) References Cited

U.S. PATENT DOCUMENTS

| | | | |
|---|---|---|---|
| 8,344,363 B2 | 1/2013 | Yamazaki et al. | |
| 8,378,391 B2 | 2/2013 | Koyama et al. | |
| 8,624,235 B2 | 1/2014 | Yamazaki et al. | |
| 8,785,919 B2 | 7/2014 | Yamazaki et al. | |
| 8,916,869 B2 | 12/2014 | Koyama et al. | |
| 9,000,429 B2 | 4/2015 | Yamazaki et al. | |
| 9,155,498 B2 | 10/2015 | Akiyama | |
| 9,165,987 B2 | 10/2015 | Yamazaki et al. | |
| 9,167,994 B2 | 10/2015 | Akiyama | |
| 9,331,112 B2 | 5/2016 | Koyama et al. | |
| 9,362,534 B2 | 6/2016 | Yamazaki et al. | |
| 9,773,814 B2 | 9/2017 | Koyama et al. | |
| 9,831,459 B2 | 11/2017 | Yamazaki et al. | |
| 10,250,247 B2 | 4/2019 | Kato et al. | |
| 10,454,059 B2 | 10/2019 | Yamazaki et al. | |
| 10,693,448 B2 | 6/2020 | Kato et al. | |
| 2003/0201447 A1* | 10/2003 | Yamazaki | H10K 50/81 257/79 |
| 2013/0075761 A1* | 3/2013 | Akiyama | H10K 65/00 257/E31.095 |
| 2017/0230041 A1 | 8/2017 | Kato et al. | |
| 2017/0352695 A1* | 12/2017 | Tsuchiya | H10K 39/32 |
| 2018/0129852 A1 | 5/2018 | Zeng et al. | |
| 2019/0242939 A1* | 8/2019 | Otto | G11C 5/146 |
| 2021/0391388 A1* | 12/2021 | Nakagawa | H10K 65/00 |

FOREIGN PATENT DOCUMENTS

| | | |
|---|---|---|
| CN | 106981503 A | 7/2017 |
| CN | 107148673 A | 9/2017 |
| DE | 102017125292 | 10/2018 |
| JP | 2004-006332 A | 1/2004 |
| JP | 2011-096668 A | 5/2011 |
| JP | 2011119711 | 6/2011 |
| JP | 2013-073965 A | 4/2013 |
| JP | 2016-115862 A | 6/2016 |
| JP | 2017-192124 A | 10/2017 |
| JP | 2018-106069 A | 7/2018 |
| KR | 2013-0033278 A | 4/2013 |
| TW | 201316495 | 4/2013 |
| WO | WO-2016/098283 | 6/2016 |

OTHER PUBLICATIONS

Written Opinion (Application No. PCT/IB2019/058363) dated Dec. 10, 2019.

* cited by examiner

FIG. 3A
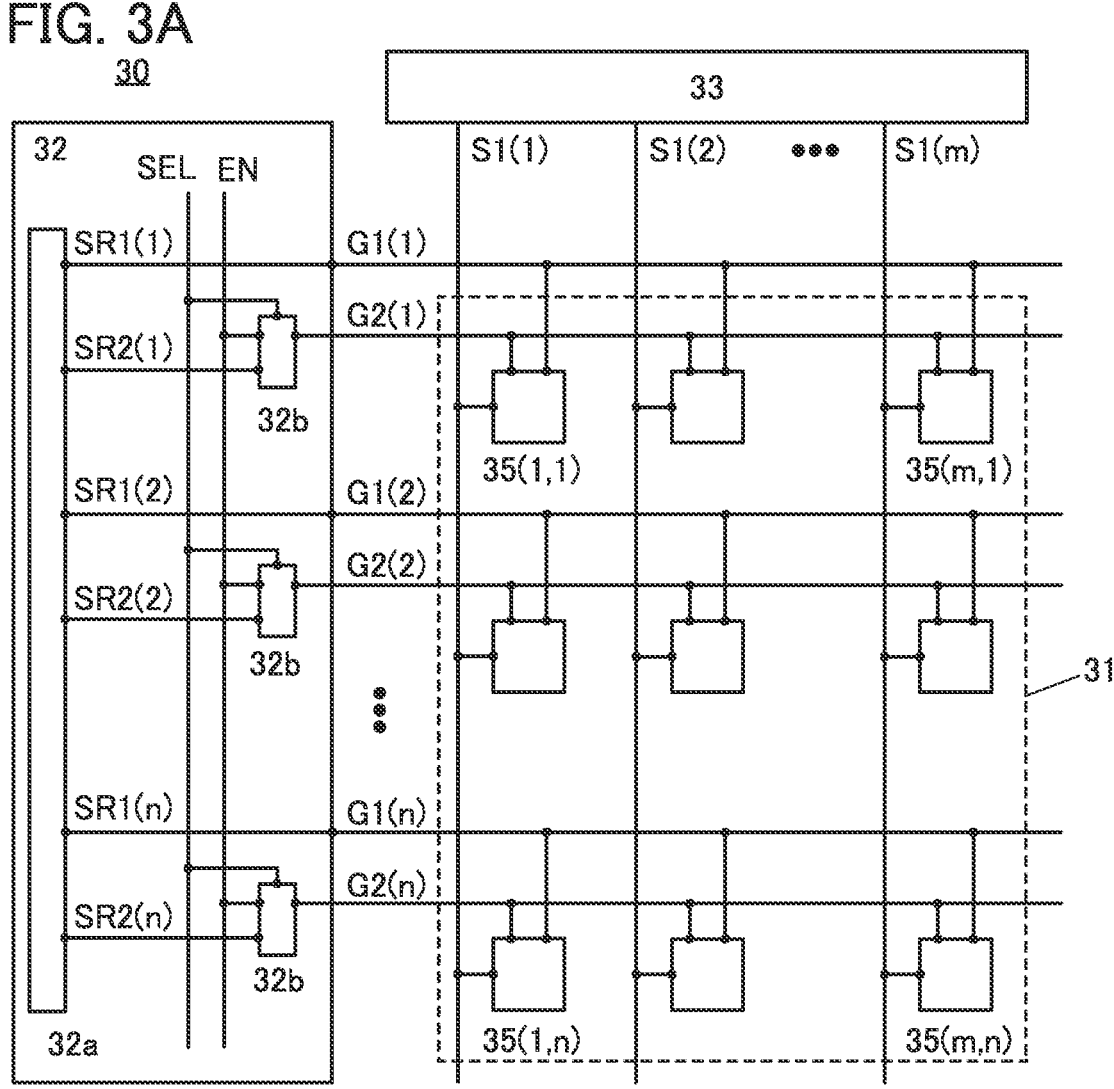
FIG. 3B1
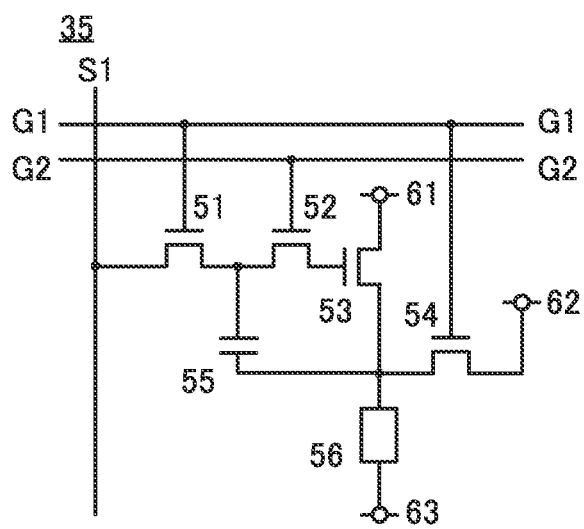
FIG. 3B2
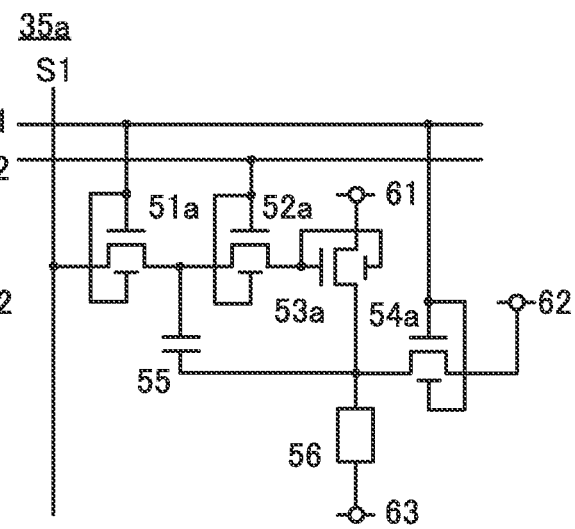

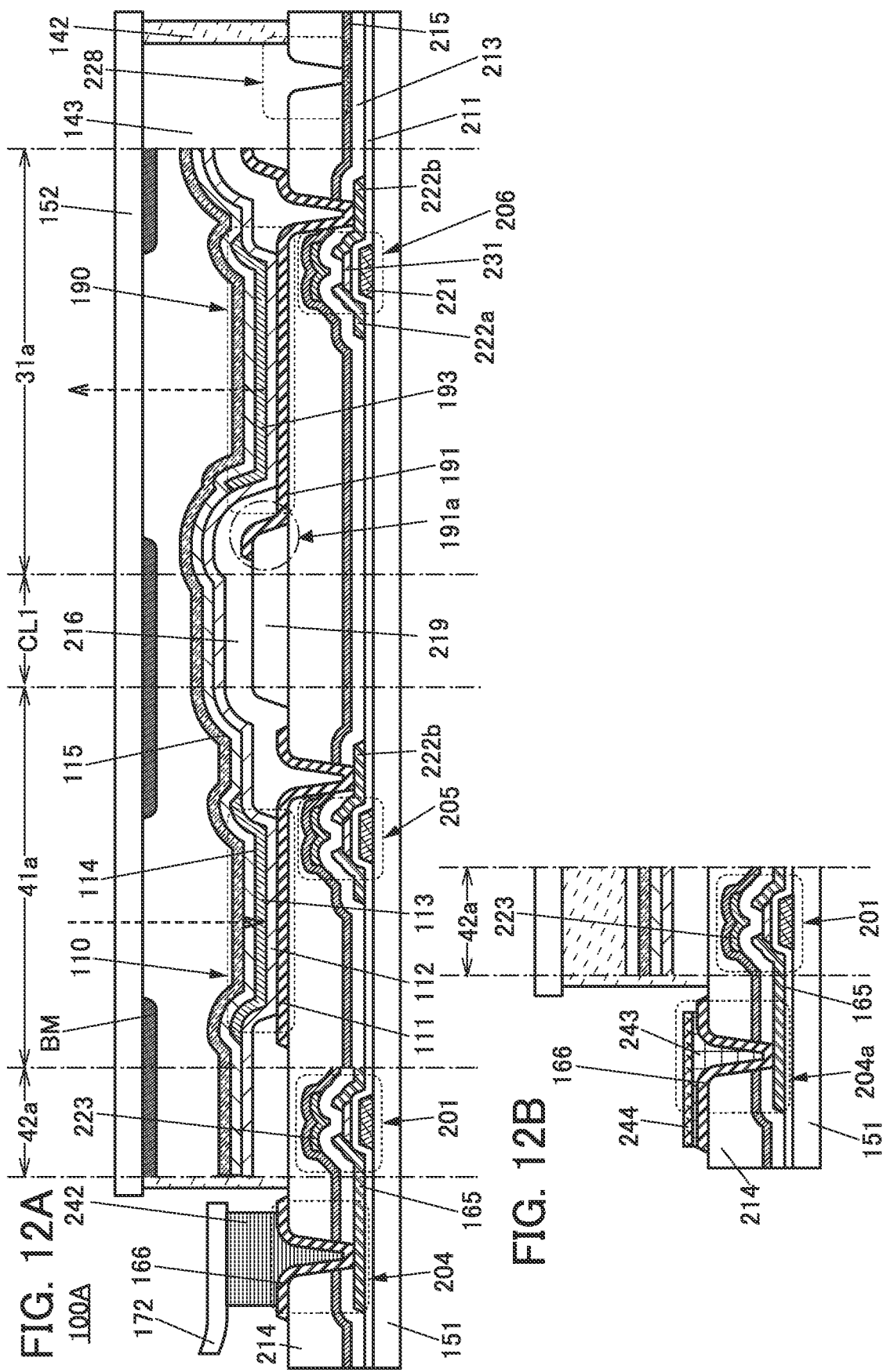

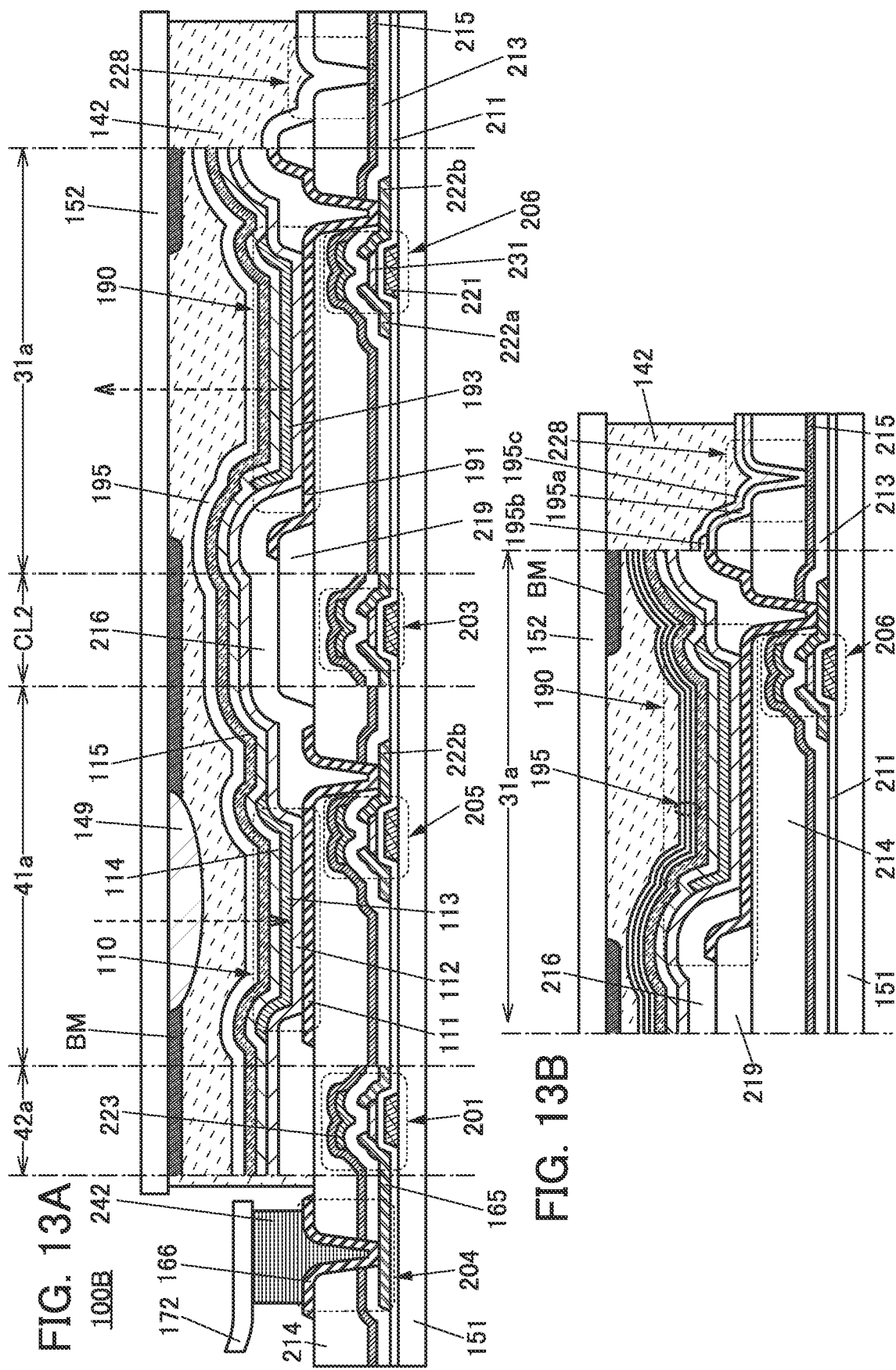

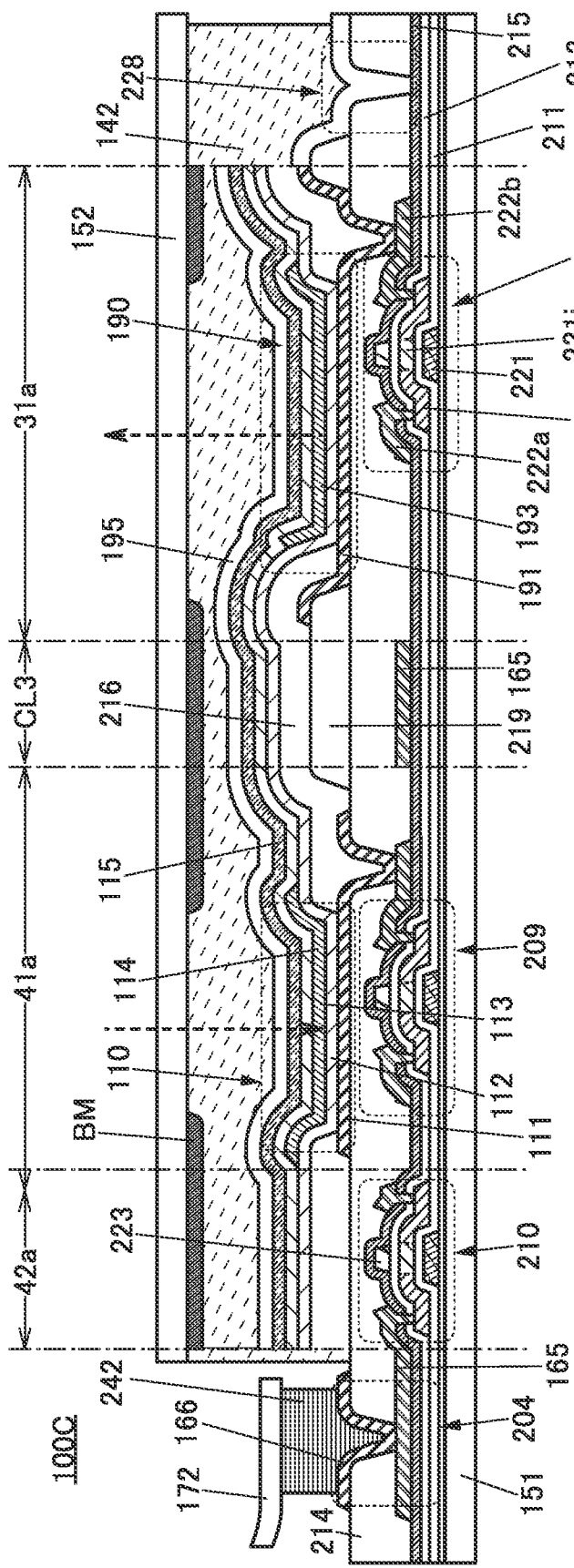

SENSOR DEVICE AND SEMICONDUCTOR DEVICE

TECHNICAL FIELD

One embodiment of the present invention relates to a sensor device and a semiconductor device.

Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a lighting device, a power storage device, a memory device, an imaging device, a communication device, a driving method thereof, and a manufacturing method thereof.

In this specification and the like, a semiconductor device generally means a device that can function by utilizing semiconductor characteristics. A transistor and a semiconductor circuit are embodiments of semiconductor devices. In some cases, a memory device, a display device, an imaging device, a communication device, or an electronic device includes a semiconductor device.

BACKGROUND ART

A technique for forming a transistor by using an oxide semiconductor thin film formed over a substrate has attracted attention. For example, an imaging device with a structure in which a transistor including an oxide semiconductor and having an extremely low off-state current is used in a pixel circuit is disclosed in Patent Document 1.

REFERENCE

Patent Document

[Patent Document 1] Japanese Published Patent Application No. 2011-119711

SUMMARY OF THE INVENTION

Problems to be Solved by the Invention

An imaging device is used not only as a means for producing an image from visible light but also for various purposes. For example, imaging devices are used for personal authentication, failure analysis, medical diagnosis, security purposes, and the like. For these purposes, short-wavelength light such as X rays, long-wavelength light such as infrared rays, and the like, as well as visible light are used in accordance with the purpose.

A physiological monitor using light having a peak wavelength of 700 nm or greater including an infrared region has been proposed as one of medical diagnostic methods for preventing or controlling lifestyle-related diseases.

It is known, as an example, that diabetes is likely to cause a variety of complications if a person's blood sugar level remains high. A method for controlling a person's blood sugar level by monitoring a blood glucose level has been proposed. The blood glucose level has an absorption peak in a wavelength range of 700 nm or greater; if a light bulb type lamp, an LED, or the like is used as a light source emitting light in the wavelength range, a device has a large size, which is a problem. In addition, light emitted to an object becomes reflected light that is scattered at a top surface of or inside the object, lowering the sensing accuracy of a sensor. Therefore, the sensor for sensing the reflected light is required to have higher sensing accuracy by increasing a light-receiving region (sensor region).

Thus, an object of one embodiment of the present invention is to provide a novel semiconductor device. Another object is to provide a novel sensor device. Another object is to provide a sensor device including a thin light source and a thin sensor. Another object is to provide a sensor device including a thin light source and a sensor for sensing, for example, light emitted from the light source and reflected by a subject. Another object is to provide a sensor device including a light-emitting element emitting light having a peak wavelength of 700 nm or greater.

Note that the description of these objects does not preclude the existence of other objects. One embodiment of the present invention does not have to achieve all these objects. Other objects are apparent from the description of the specification, the drawings, the claims, and the like, and other objects can be derived from the description of the specification, the drawings, the claims, and the like.

Means for Solving the Problems

One embodiment of the present invention relates to a semiconductor device including a sensor device.

One embodiment of the present invention is a semiconductor device including a sensor device, a processor, and a communication device. The sensor device includes a first pixel and a second pixel formed over a substrate. The first pixel includes a light-emitting element and a first transistor. The second pixel includes a sensor element having a photoelectric conversion function and a second transistor. Light emitted from the light-emitting element has a peak wavelength and a range of wavelength sensed by the sensor element includes the peak wavelength. The first transistor and the second transistor include the same element in their semiconductor layers. A pixel electrode included in the light-emitting element has a function of being electrically connected to the first transistor and a function of blocking diffusion light to the sensor element. Light sensed by the sensor element is subjected to arithmetic operation in the processor. In the semiconductor device, the communication device transmits the result of the arithmetic operation.

Another embodiment of the present invention is a sensor device including a first pixel and a second pixel formed over a substrate. The first pixel includes a light-emitting element and a first transistor. The second pixel includes a sensor element having a photoelectric conversion function and a second transistor. Light emitted from the light-emitting element has a peak wavelength and a range of wavelength sensed by the sensor element includes the peak wavelength. The first transistor and the second transistor include the same element in their semiconductor layers. In the sensor device, a pixel electrode included in the light-emitting element has a function of being electrically connected to the first transistor and a function of blocking diffusion light to the sensor element.

The substrate may be flexible.

The peak wavelength of the light-emitting element is preferably greater than or equal to 700 nm and less than or equal to 9000 nm.

It is preferable that the light-emitting element include a first organic compound and a common layer, and the sensor element include a second organic compound and the common layer.

It is preferable that a region including no conductive layer be provided between the first pixel and the second pixel.

It is preferable that the first transistor and the second transistor each include a metal oxide in the semiconductor layer and the metal oxide include In, Zn, and M (M is Al, Ti, Ga, Sn, Y, Zr, La, Ce, Nd, or Hf). It is preferable that the first transistor or the second transistor include a back gate.

Effect of the Invention

According to one embodiment of the present invention, a novel semiconductor device can be provided. Alternatively, a novel sensor device can be provided. Alternatively, a sensor device including a thin light source and a thin sensor can be provided. Alternatively, a sensor device including a thin light source and a sensor for sensing light emitted from the light source and reflected by a subject can be provided. Alternatively, a sensor device including a light-emitting element emitting light having a peak wavelength of 700 nm or greater can be provided.

BRIEF DESCRIPTION OF THE DRAWINGS

FIG. 3A is a circuit diagram illustrating a pixel array. FIG. 3B1 and FIG. 3B2 are circuit diagrams each illustrating a pixel.

FIG. 4C1 and FIG. 4C2 are circuit diagrams illustrating a circuit 46 and a circuit 46a.

FIG. 12A and FIG. 12B are cross-sectional views each illustrating an example of a sensor device.

FIG. 13A and FIG. 13B are cross-sectional views each illustrating an example of a sensor device.

FIG. 14A and FIG. 14B are cross-sectional views each illustrating an example of a sensor device.

MODE FOR CARRYING OUT THE INVENTION

Figure 1:
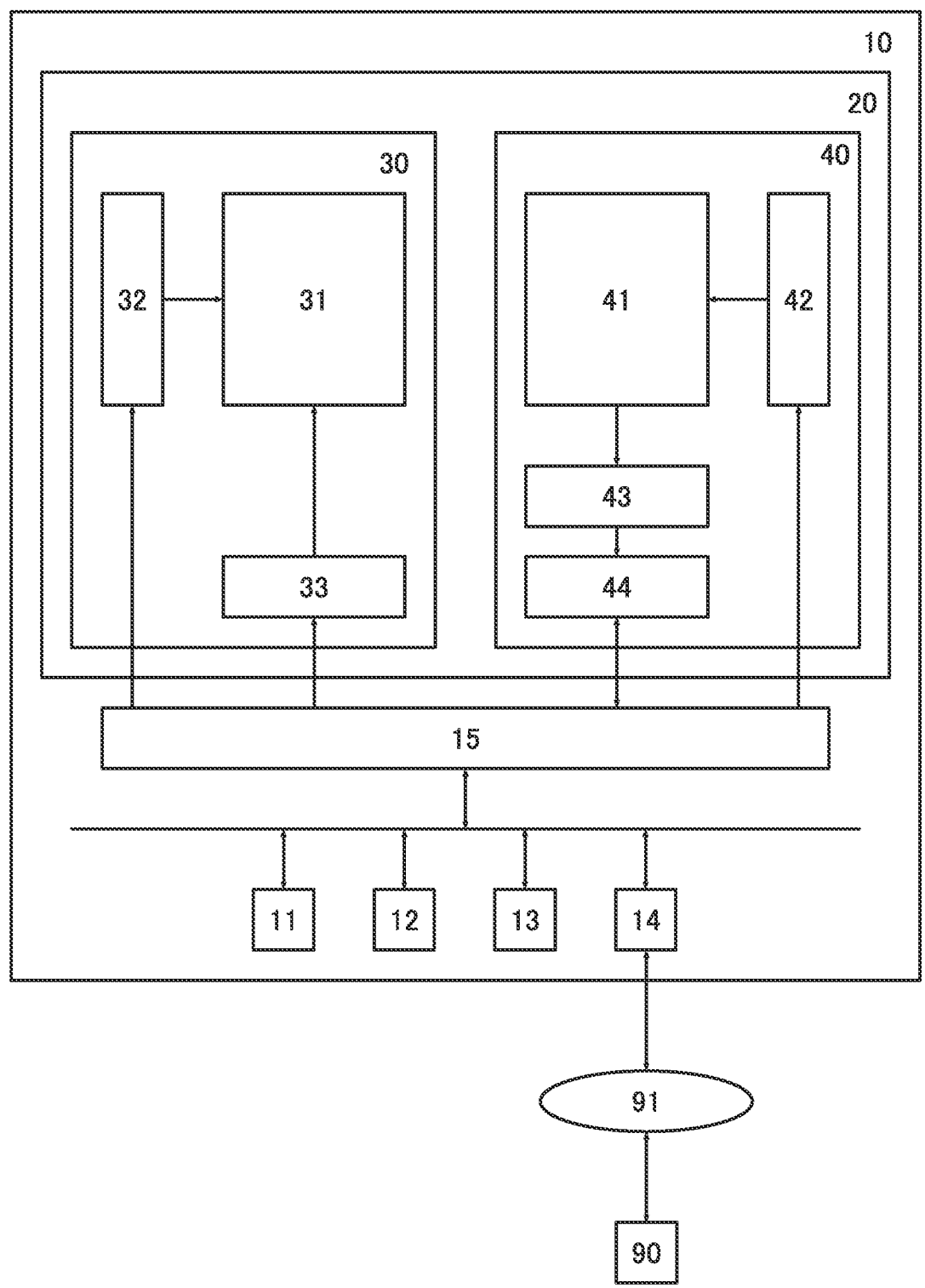
FIG. 1 is a block diagram illustrating a semiconductor device.

Embodiments are described in detail with reference to the drawings. Note that the present invention is not limited to the following description, and it will be readily understood by those skilled in the art that modes and details of the present invention can be modified in various ways without departing from the spirit and scope. Therefore, the present invention should not be interpreted as being limited to the descriptions of the embodiments below. Note that in structures of the invention described below, the same portions or portions having similar functions are denoted by the same reference numerals in different drawings, and the description thereof is not repeated in some cases. The same components are denoted by different hatching patterns in different drawings, or the hatching patterns are omitted in some cases.

Hereinafter, embodiments will be described with reference to the drawings. Note that the embodiments can be implemented with many different modes, and it will be readily understood by those skilled in the art that modes and details thereof can be changed in various ways without departing from the spirit and scope thereof. Thus, the present invention should not be interpreted as being limited to the descriptions of the embodiments below.

In the drawings, the size, the layer thickness, or the region is exaggerated for clarity in some cases. Therefore, they are not limited to the illustrated scale. Note that the drawings are schematic views illustrating ideal examples, and embodiments of the present invention are not limited to shapes or values shown in the drawings.

Furthermore, it is noted that ordinal numbers such as "first", "second", and "third" used in this specification are used in order to avoid confusion among components, and the terms do not limit the components numerically.

In this specification, terms for describing arrangement, such as "over" and "under", are used for convenience in describing a positional relation between components with reference to drawings. The positional relation between components is changed as appropriate in accordance with a direction in which each component is described. Thus, without limitation to terms described in this specification, the description can be changed appropriately depending on the situation.

In this specification and the like, a transistor is an element having at least three terminals of a gate, a drain, and a source. The transistor has a channel formation region between the drain (a drain terminal, a drain region, or a drain electrode) and the source (a source terminal, a source region, or a source electrode), and can make current flow between the source and the drain through the channel formation region. Note that in this specification and the like, a channel formation region refers to a region through which current mainly flows.

Furthermore, functions of a source and a drain might be switched when a transistor of opposite polarity is employed or a direction of current flow is changed in circuit operation, for example. Thus, the terms of source and drain are interchangeably used in this specification and the like.

In this specification and the like, "electrically connected" includes the case where connection is made through an "object having any electric function". There is no particular limitation on the "object having any electric function" as long as electric signals can be transmitted and received between components that are connected through the object. Examples of the "object having any electric function" include a switching element such as a transistor, a resistor, an inductor, a capacitor, and other elements with a variety of functions as well as electrodes and wirings formed of different conductive layers.

In this specification and the like, "parallel" indicates a state where two straight lines are placed at an angle of greater than or equal to −10° and less than or equal to 10°.

Thus, the case where the angle is greater than or equal to −5° and less than or equal to 5° is also included. Moreover, "perpendicular" indicates a state where two straight lines are placed at an angle of greater than or equal to 80° and less than or equal to 100°. Thus, the case where the angle is greater than or equal to 85° and less than or equal to 95° is also included.

Moreover, in this specification and the like, the term "film" and the term "layer" can be interchanged with each other. For example, the term "conductive layer" can be changed into the term "conductive film" in some cases. Moreover, the term "insulating film" can be changed into the term "insulating layer" in some cases.

Furthermore, unless otherwise specified, off-state current in this specification and the like refers to drain current of a transistor in an off state (also referred to as a non-conducting state or a cutoff state). Unless otherwise specified, the off state of an n-channel transistor refers to a state where the voltage Vgs between its gate and source is lower than the threshold voltage Vth, and the off state of a p-channel transistor refers to a state where the voltage Vgs between its gate and source is higher than the threshold voltage Vth. For example, the off-state current of an n-channel transistor sometimes refers to a drain current at the time when the voltage Vgs between its gate and source is lower than the threshold voltage Vth.

The off-state current of a transistor depends on Vgs in some cases. Thus, the off-state current of a transistor being lower than or equal to I sometimes means that there is Vgs with which the off-state current of the transistor becomes lower than or equal to I. The off-state current of a transistor sometimes refers to the off-state current in an off state at predetermined Vgs, in an off state at Vgs in a predetermined range, in an off state at Vgs with which sufficiently reduced off-state current is obtained, or the like.

As an example, the assumption is made of an n-channel transistor where the threshold voltage Vth is 0.5 V, and the drain current at Vgs of 0.5 V is $1 \times 10^{-9}$ A, the drain current at Vgs of 0.1 V is $1 \times 10^{-13}$ A, the drain current at Vgs of −0.5 V is $1 \times 10^{-19}$ A, and the drain current at Vgs of −0.8 V is $1 \times 10^{-22}$ A. The drain current of the transistor is lower than or equal to $1 \times 10^{-19}$ A at Vgs of −0.5 V or at Vgs in the range of −0.5 V to −0.8 V; therefore, it is sometimes said that the off-state current of the transistor is lower than or equal to $1 \times 10^{-19}$ A. Since there is Vgs at which the drain current of the transistor is lower than or equal to $1 \times 10^{-22}$ A, it is sometimes said that the off-state current of the transistor is lower than or equal to $1 \times 10^{-22}$ A.

In this specification and the like, the off-state current of a transistor having a channel width W is sometimes represented by the value of flowing current per channel width W. Alternatively, it is sometimes represented by the value of flowing current per given channel width (e.g., 1 µm). In the latter case, the off-state current is sometimes represented by the unit with the dimension of current per length (e.g., A/µm).

The off-state current of a transistor depends on temperature in some cases. Unless otherwise specified, the off-state current in this specification sometimes refers to off-state current at room temperature, 60° C., 85° C., 95° C., or 125° C. Alternatively, the off-state current sometimes refers to off-state current at a temperature at which reliability of a semiconductor device or the like including the transistor is ensured or a temperature at which the semiconductor device or the like including the transistor is used (e.g., any temperature in the range of 5° C. to 35° C.). The off-state current of the transistor being lower than or equal to I sometimes means that there is Vgs at which the off-state current of a transistor is lower than or equal to I at room temperature, 60° C., 85° C., 95° C., 125° C., a temperature at which reliability of a semiconductor device or the like including the transistor is ensured, or a temperature at which the semiconductor device or the like including the transistor is used (e.g., any temperature in the range of 5° C. to 35° C.).

The off-state current of a transistor depends on the voltage Vds between its drain and source in some cases. Unless otherwise specified, the off-state current in this specification sometimes refers to an off-state current at Vds of 0.1 V, 0.8 V, 1 V, 1.2 V, 1.8 V, 2.5 V, 3 V, 3.3 V, 10 V, 12 V, 16 V, or 20 V. Alternatively, the off-state current sometimes refers to off-state current at Vds at which reliability of a semiconductor device or the like including the transistor is ensured or Vds used in the semiconductor device or the like including the transistor. The off-state current of the transistor being lower than or equal to I sometimes means that there is Vgs at which the off-state current of a transistor is lower than or equal to I at Vds of 0.1 V, 0.8 V, 1 V, 1.2 V, 1.8 V, 2.5 V, 3 V, 3.3 V, 10 V, 12 V, 16 V, or 20 V, at Vds at which reliability of a semiconductor device or the like including the transistor is ensured, or at Vds used in the semiconductor device or the like including the transistor.

In the above description of the off-state current, the drain may be replaced with the source. That is, the off-state current sometimes refers to a current that flows through a source of a transistor in an off state.

In this specification and the like, leakage current sometimes expresses the same meaning as off-state current. Furthermore, in this specification and the like, the off-state current sometimes refers to current that flows between a source and a drain of a transistor in an off state, for example.

Note that voltage refers to a difference between potentials of two points, and a potential refers to electrostatic energy (electric potential energy) of a unit charge at a given point in an electrostatic field. In general, a difference between a potential of one point and a reference potential (e.g., a ground potential) is merely called a potential or voltage, and a potential and voltage are used as synonyms in many cases. Therefore, in this specification, a potential may be rephrased as a voltage and a voltage may be rephrased as a potential unless otherwise specified.

Embodiment 1

In this embodiment, a semiconductor device of one embodiment of the present invention will be described.

The semiconductor device includes a sensor device, a processor, a memory, a battery, and a communication device. The sensor device includes a first region and a second region formed over a substrate. Note that the substrate may be flexible. A plurality of first pixels are arranged in matrix in the first region and a plurality of second pixels are arranged in matrix in the second region. The first pixels each include a light-emitting element and a first transistor. The second pixels each include a sensor element having a photoelectric conversion function and a second transistor.

The first transistor and the second transistor include the same element in their semiconductor layers.

Light emitted from the light-emitting element has a peak wavelength and a range of wavelength sensed by the sensor element includes the peak wavelength. The peak wavelength of the light-emitting element is preferably greater than or equal to 700 nm and less than or equal to 9000 nm.

Here, the case where an object is sensed or inspected with the semiconductor device of one embodiment of the present invention is described. In the case where an object (e.g., a material) has a property of absorbing light in a specific wavelength range, a peak wavelength of the light-emitting element is preferably included in the specific wavelength range. The object absorbs light having the peak wavelength when reflecting or transmitting emitted light. In the case where the sensor element senses reflected light or transmitted light from an object portion, the sensor element can sense light having the peak wavelength. The object absorbs light in a plurality of different wavelength ranges in some cases. Thus, the light-emitting element preferably emits light having peak wavelengths in different wavelength ranges. Furthermore, the sensor element is preferably capable of sensing the light having peak wavelengths in different wavelength ranges. The object can be accurately sensed or inspected by sensing light having peak wavelengths in different wavelength ranges.

It is known, as an example, that glucose in a vein has a first wavelength range in which light having a wavelength of 1600 nm and its vicinity is easily absorbed and a second wavelength range in which light having a wavelength of 6000 nm to 9000 nm is easily absorbed. Thus, the amount of glucose in a vein can be sensed in such a manner that the sensor element senses reflected light of light emitted to the vein. The reflected light sensed by the sensor element is subjected to arithmetic operation in the processor and converted into a blood sugar level or the like. The communication device can transmit the converted result to a server, a personal computer, or a portable information terminal such as a smartphone via a network.

As another example, light having a wavelength of 760 nm and its vicinity is easily absorbed by hemoglobin in a vein; thus, the position of the vein can be sensed by making an image from received reflected light or the like from a palm, a finger, or the like. This operation can be utilized for biometric authentication. Moreover, with the use of infrared light having an appropriate wavelength, the operation can also be utilized for non-destructive testing such as foreign body inspection of foods or failure analysis of industrial products.

The light-emitting element can achieve a thin light source by including a first organic compound and a common layer. The sensor element can achieve a thin sensor by including a second organic compound and the common layer.

Since the light-emitting element and the sensor element are formed over the same substrate, a region, a layer, or the like having a light-blocking function is preferably provided between the light-emitting element and the sensor element. In addition, for reducing diffused reflection by a conductive layer, a region including no conductive layer is preferably provided between the first region and the second region.

Next, the semiconductor device of one embodiment of the present invention will be described with reference to drawings.

One embodiment of the present invention is a sensor device including a light-emitting element. A sensor element receives light that is emitted from the light-emitting element and reflected by a subject, for example. An organic light-emitting element is used as the light-emitting element and an organic sensor element is used as the sensor element; thus, a sensor device with a thin light source can be formed. Note that the sensor element has a photoelectric conversion function.

FIG. 1 is a block diagram illustrating a semiconductor device of one embodiment of the present invention. The semiconductor device 10 includes a sensor device 20, a processor 11, a memory 12, a battery 13, a communication device 14, and an image processing circuit 15. The sensor device 20 includes a region 30 and a region 40.

The image processing circuit 15 can control driving timing of the sensor device 20. The processor 11 can perform arithmetic operation of sensing data sensed by the sensor device 20 and supply the result of the arithmetic operation to the communication device 14. The communication device 14 can transmit the result of the arithmetic operation to a server 90 via a network 91. Note that the communication device 14 may transmit the result to a portable information terminal such as a smartphone, a personal computer, or the like via the network 91.

The region 30 includes a light-emitting region 31, a circuit 32 (gate driver), and a circuit 33 (source driver). The light-emitting region 31 includes a plurality of first pixels, and the plurality of first pixels are arranged in matrix. Note that the first pixels are to be described in detail with reference to FIG. 3A, FIG. 3B1, and FIG. 3B2. The circuit 32 can select from the plurality of first pixels. The circuit 33 can supply emission data in accordance with emission intensity of light-emitting elements to the first pixels selected by the circuit 32.

The region 40 includes a sensor region 41, a circuit 42 (row driver), a circuit 43 (analog digital converter), and a circuit 44 (column driver). The sensor region 41 includes a plurality of second pixels, and the plurality of second pixels are arranged in matrix. Note that the second pixels are to be described in detail with reference to FIG. 4A, FIG. 4B, FIG. 4C1, and FIG. 4C2. The circuit 42 can select from the plurality of second pixels. A sensor element included in the second pixel can convert light into voltage that is an analog signal owing to a photoelectric conversion function. The circuit 43 converts the analog signal sensed by the second pixel into a digital signal as sensing data. The circuit 44 can supply the sensing data to the image processing circuit 15. The image processing circuit 15 can supply the sensing data to the processor 11.

Figure 2:
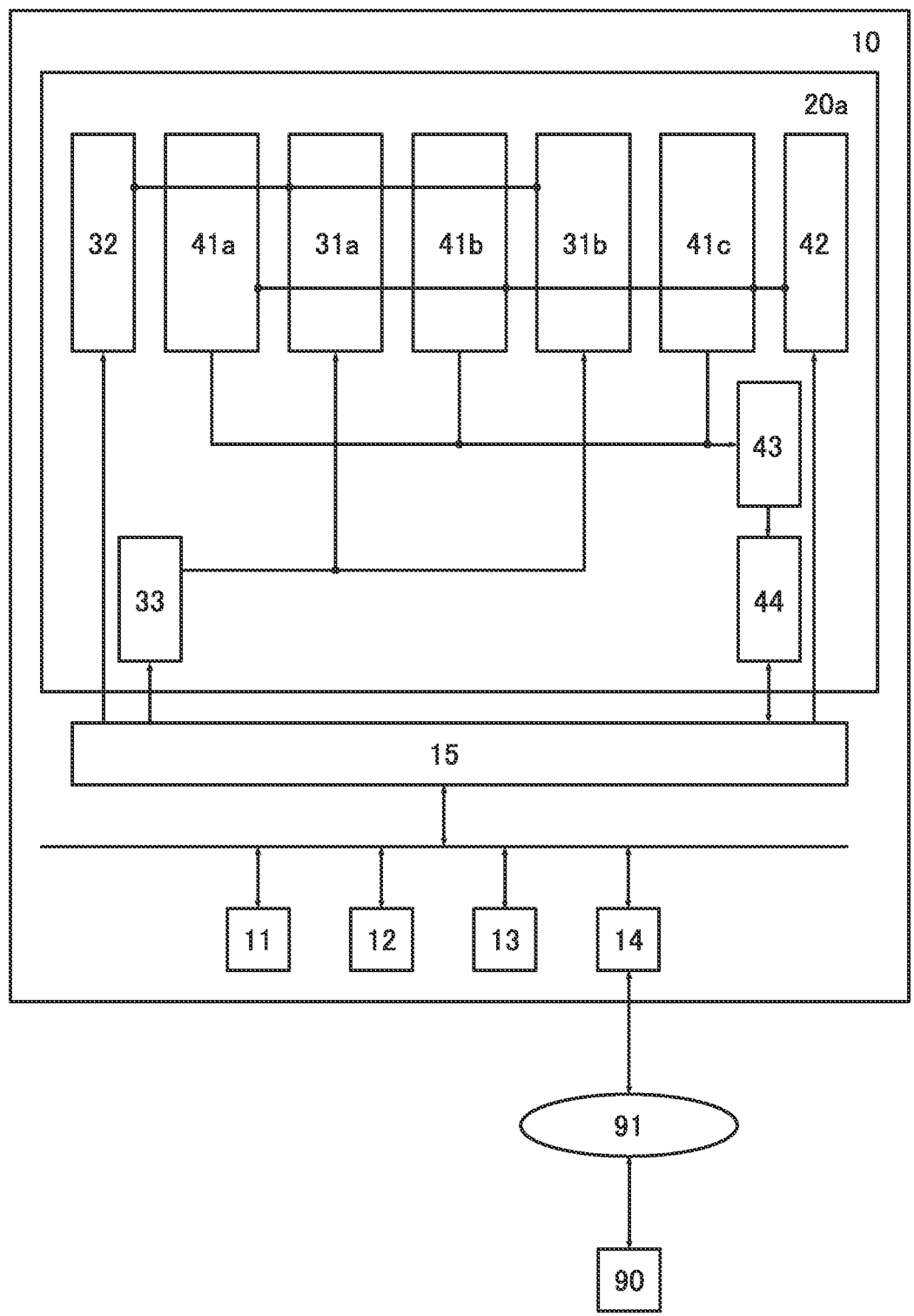
FIG. 2 is a block diagram illustrating a semiconductor device.

FIG. 2 is a block diagram illustrating the semiconductor device 10 including a sensor device 20a having another structure. The sensor device 20a includes a light-emitting region 31a, a light-emitting region 31b, a sensor region 41a, a sensor region 41b, and a sensor region 41c. The circuit 32 and the circuit 33 can drive the light-emitting region 31a and the light-emitting region 31b, and the circuit 42 and the circuit 43 can drive the sensor region 41a, the sensor region 41b, and the sensor region 41c.

The light-emitting region 31a may emit light having a peak wavelength different from that of light of the light-emitting region 31b. Alternatively, the light-emitting region 31a may emit light having the same peak wavelength as the light-emitting region 31b.

The sensor region 41a can sense light in a different wavelength range from the sensor region 41b or the sensor region 41c. For example, the sensor region 41a can sense light having the peak wavelength emitted from the light-emitting region 31a. The sensor region 41c can sense light having the peak wavelength emitted from the light-emitting region 31b. The sensor region 41b can sense light having the peak wavelength emitted from either the light-emitting region 31a or the light-emitting region 31b. Alternatively, the sensor region 41b can sense both light having the peak wavelength emitted from the light-emitting region 31a and light having the peak wavelength emitted from the light-emitting region 31b.

As described above, a sensor device including light sources emitting light having a plurality of different peak wavelengths and sensor regions sensing light having a plurality of different peak wavelengths is suitable for appropriately sensing an object having absorption bands in different wavelength ranges, such as glucose. For example, in the case where an object to be sensed is glucose, glucose has a first wavelength range in which light having a wavelength of 1600 nm and its vicinity is absorbed and a second wavelength range in which light having a wavelength of 6000 nm to 9000 nm is absorbed. Note that the absorption intensities are known to be different in the wavelength ranges. That is, first sensing data sensed in the first wavelength range and second sensing data sensed in the second wavelength range are compared with each other or subjected to arithmetic operation, whereby the amount or the content ratio of glucose that is the object can be accurately sensed.

FIG. 3A is a circuit diagram illustrating a pixel array included in the region 30. The region 30 includes the light-emitting region 31, the circuit 32, and the circuit 33. The light-emitting region 31 includes a pixel 35(1,1) to a pixel 35(*m,n*) arranged in matrix, a wiring G1(1) to a wiring G1(*n*), a wiring G2(1) to a wiring G2(*n*), and a wiring S1(1) to a wiring S1(*m*). The circuit 32 includes a shift register 32*a*, a plurality of selector circuits 32*b*, a wiring SR1(1) to a wiring SR1(*n*), a wiring SR2(1) to a wiring SR2(*n*), a wiring SEL, and a wiring EN. Note that m and n are each an integer of 2 or more. Note that the shift register 32*a* may include a decoder circuit.

Each pixel 35 is electrically connected to the wiring G1, the wiring G2, and the wiring S1.

The shift register 32*a* is electrically connected to the wirings G1 through the wirings SR1. The wiring SEL is electrically connected to first input terminals of the selector circuits 32*b*. The shift register 32*a* is electrically connected to second input terminals of the selector circuits 32*b* through the wirings SR2. The wiring EN is electrically connected to third input terminals of the selector circuits 32*b*. Output terminals of the selector circuits 32*b* are electrically connected to the wirings G2.

A signal supplied to the wiring SEL allows either one of a signal supplied to the second input terminal of the selector circuit 32*b* and a signal supplied to the third input terminal to be supplied to the wiring G2 as an output signal of the selector circuit 32*b*. The signal supplied to the second input terminal is an output signal of the shift register 32*a* supplied to the wiring SR2. The signal supplied to the third input terminal is a signal supplied to the wiring EN. For example, in the case where a signal "L" is supplied to the wiring SEL, the selector circuit 32*b* can output an output signal of the shift register 32*a* to the wiring G2. In the case where a signal "H" is supplied to the wiring SEL, the selector circuit 32*b* can output a signal supplied to the wiring EN to the wiring G2.

Note that in the case where the signal "H" is supplied to the wiring SEL, a signal supplied to the wiring EN can be output concurrently to the wiring G2(1) to the wiring G2(*n*). Accordingly, the pixel 35(1,1) to the pixel 35(*m,n*) can concurrently emit light or stop emitting light. That is, light emitted instantaneously like light from a flash of a camera can be generated. Note that the intensities of light emitted from the pixel 35(1,1) to the pixel 35(*m,n*) are determined in accordance with light emission data supplied to the respective pixels 35 through the wiring S1(1) to the wiring S1(*m*).

The pixel 35 is described using a circuit diagram of FIG. 3B1. The pixel 35 includes a transistor 51 to a transistor 54, a capacitor 55, and a light-emitting element 56. The wiring G1 is electrically connected to a gate of the transistor 51 and a gate of the transistor 54. The wiring G2 is electrically connected to a gate of the transistor 52. The wiring S1 is connected to one of a source and a drain of the transistor 51. The other of the source and the drain of the transistor 51 is electrically connected to one of a source and a drain of the transistor 52 and one electrode of the capacitor 55. The other of the source and the drain of the transistor 52 is electrically connected to a gate of the transistor 53. One of a source and a drain of the transistor 53 is electrically connected to a wiring 61. The other of the source and the drain of the transistor 53 is connected to one electrode of the light-emitting element 56, one electrode of the transistor 54, and the other electrode of the capacitor 55. The other of the source and the drain of the transistor 54 is electrically connected to a wiring 62. The other electrode of the light-emitting element 56 is electrically connected to a wiring 63.

A signal supplied to the wiring G1 can control turning on or off of the transistor 51 and the transistor 54. The transistor 51 functions as a selection switch of the pixel. In a period during which the transistor 51 is in an on state, the transistor 54 can supply a potential supplied to the wiring 62 to the other electrode of the capacitor 55. Note that the potential supplied to the wiring 62 is preferably a potential that does not make the light-emitting element 56 emit light. In a period during which the potential of the other of the source and the drain of the transistor 53 is fixed by the potential supplied to the wiring 62, light emission data is supplied to the one electrode of the capacitor 55 through the wiring S1. Note that the gate of the transistor 54 may be connected to a different wiring G3. By providing the wiring G3, the transistor 51 and the transistor 54 can be controlled to turn on or off at different timings.

A signal supplied to the wiring G2 can control the timing at which light emission data retained in the capacitor 55 is supplied to the gate of the transistor 53. Note that it is preferable that the same potential as the potential of the other of the source and the drain of the transistor 53 be supplied to the gate of the transistor 53 before light emission data is supplied to the capacitor 55.

An OS transistor including a metal oxide in a semiconductor layer can be used as each of the transistor 51 to the transistor 54. The OS transistor has a feature of an extremely low off-state current. When OS transistors are used as the transistor 51 to the transistor 54, a period during which charge can be retained in the capacitor 55 can be elongated greatly.

Alternatively, the transistor 53 may include a semiconductor layer different from that in the transistor 51. For example, the transistor 53 may be a Si transistor including Si in its semiconductor layer. Examples of the Si transistor include a transistor including amorphous silicon and a transistor including crystalline silicon (typically, low-temperature polysilicon, single crystal silicon, or the like). In the case where the transistor 53 is a Si transistor, the emission intensity of the light-emitting element 56 can be increased easily. Moreover, in the case where the transistor 51 is an OS transistor, a period during which charge can be retained in the capacitor 55 can be elongated greatly owing to extremely low off-state current.

As another example, the transistor 53 may include a semiconductor layer different from that in the transistor 51. The transistor 51 may be a Si transistor including Si in its semiconductor layer. When the transistor 51 is a Si transistor, responsiveness of the selection switch value is improved. Moreover, in the case where the transistor 53 is an OS transistor, the channel length of the transistor can be reduced. When the channel length of the transistor is reduced, the size of the pixel can be reduced. That is, the resolution of the light-emitting region 31 can be increased.

In the above-described case where the transistor 53 includes a semiconductor layer different from that in the transistor 51, the transistor 52 or the transistor 54 may be an OS transistor. In the case where the transistor 52 is an OS transistor, owing to its low off-state current, the transistor 52 functions as a switch for reducing leakage of current of the light emission data retained in the capacitor 55 to the gate of the transistor 53. Thus, light emission of the light-emitting element 56 due to the leakage current can be inhibited. Furthermore, in the case where the transistor 54 is an OS transistor, owing to its low off-state current, the transistor 54 can function as a switch for inhibiting a change in the emission intensity of the light-emitting element 56 due to leakage current through the transistor 54.

For another example, in the case where the transistor 53 includes a semiconductor layer different from that in the transistor 51, the transistor 52 or the transistor 54 may be a Si transistor. With the use of the Si transistor, responsiveness of the switch is improved. In addition, when the channel length and the channel width of the transistor are reduced, parasitic capacitance of the transistor can be reduced and the resolution of the light-emitting region 31 can be increased.

FIG. 3B2 illustrates an example in which a transistor 51a to a transistor 54a include back gates in a pixel 35a. The back gates are electrically connected to gates of the respective transistors. Note that the connection destinations of the back gates are not limited. A back gate may be electrically connected to a source of a transistor, or back gates of a plurality of transistors may be connected to another wiring and the plurality of transistors may be collectively controlled by the wiring.

Figure 4A:
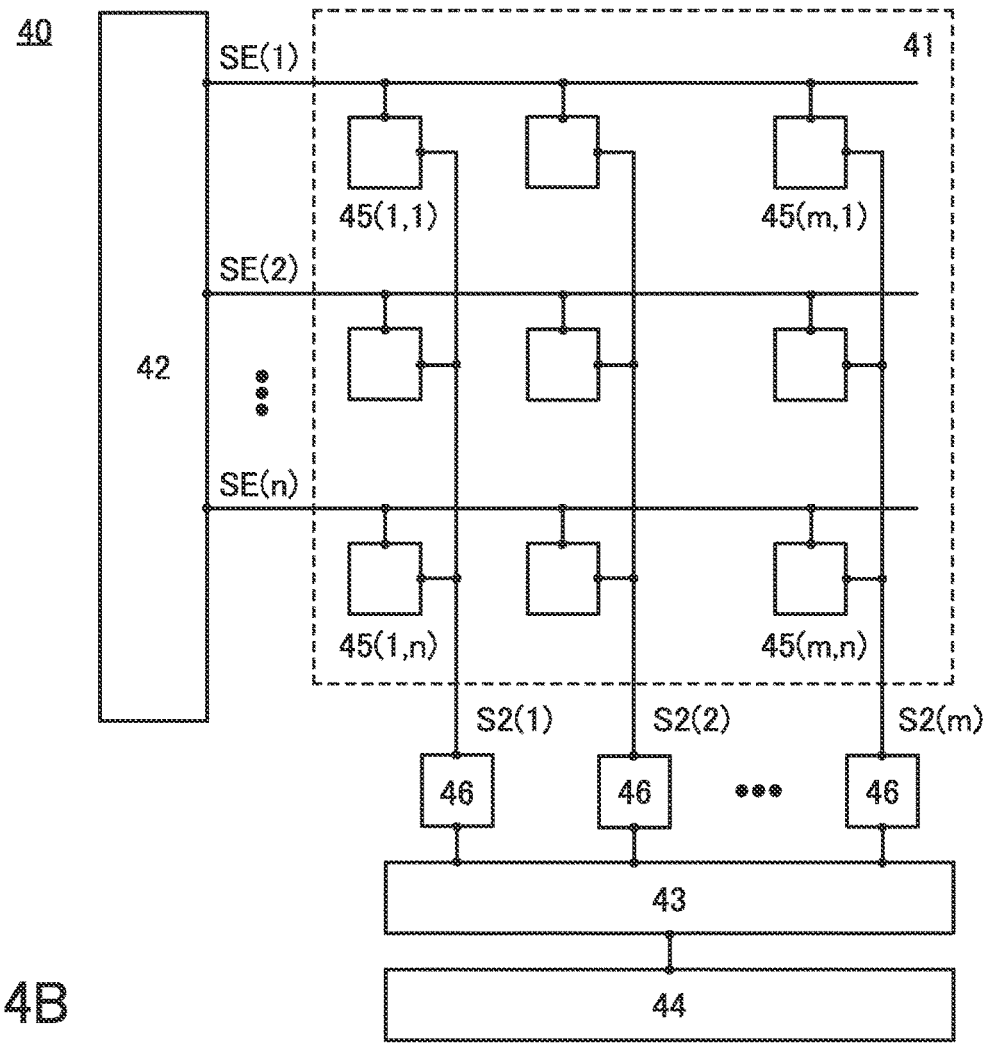
FIG. 4A is a circuit diagram illustrating a pixel array.

The pixel array included in the region 40 is described with a circuit diagram in FIG. 4A. The region 40 includes the sensor region 41, the circuit 42, the circuit 43, the circuit 44, and a circuit 46. The sensor region 41 includes a pixel 45(1,1) to a pixel 45(m,n) arranged in matrix, a wiring SE(1) to a wiring SE(n), and a wiring S2(1) to a wiring S2(m). The circuit 46 is provided for each wiring S2. Alternatively, one circuit 46 may be provided for a plurality of wirings S2.

The pixel 45 is electrically connected to the wiring SE and the wiring S2. The pixel 45 is electrically connected to the circuit 46 through the wiring S2. The circuit 46 is electrically connected to the circuit 43. The circuit 43 is electrically connected to the circuit 44. The circuit 44 is electrically connected to the image processing circuit 15.

The circuit 42 functions as a row decoder and preferably includes one of a decoder and a shift register. The circuit 42 can select a given pixel 45 through the wiring SE. Each of the pixels 45 includes a sensor element. The sensor element photoelectrically converts incident light into a voltage that is analog data. That is, the pixel 45 can convert light into a voltage to supply it to the circuit 46 as output data.

The circuit 46 is a source follower circuit for supplying the output data of the pixel 45 to the circuit 43. The circuit 43 performs correlated double sampling on the output data supplied through the source follower circuit. Furthermore, the circuit 43 has a function of converting the output data subjected to the double sampling into digital data. The circuit 44 can transfer the digital data to the image processing circuit 15. The circuit 44 functions as a column decoder.

Figure 4B:
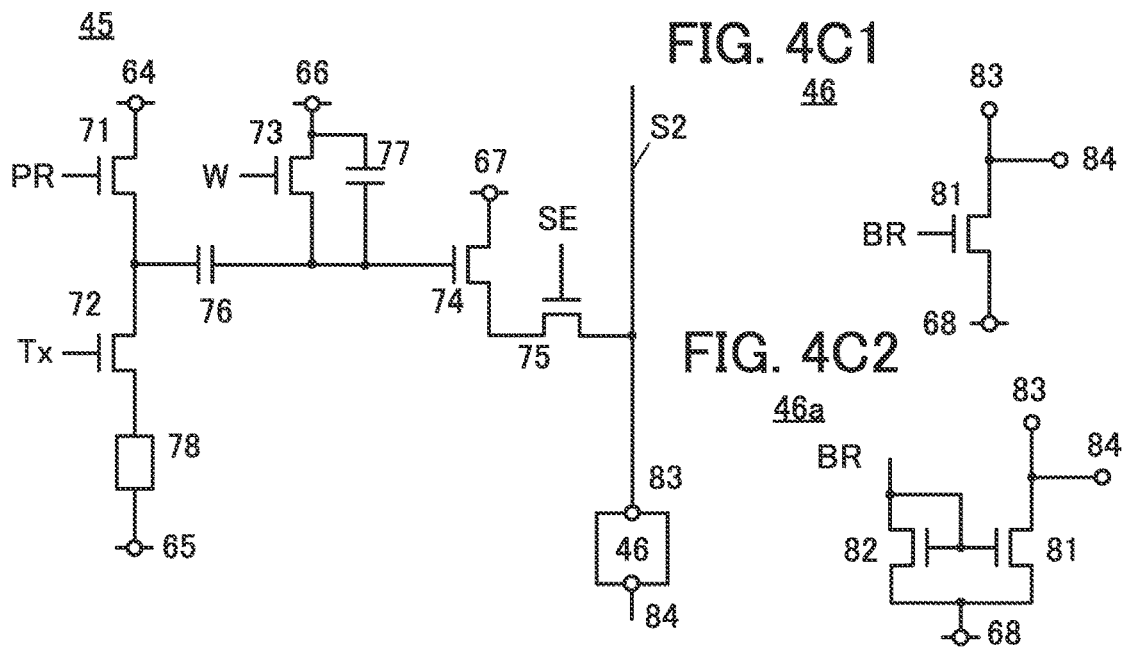
FIG. 4B is a circuit diagram illustrating a pixel.

The pixel 45 is described using a circuit diagram of FIG. 4B. Note that the pixel 45 is electrically connected to a wiring 64 to a wiring 67.

The pixel 45 includes a transistor 71 to a transistor 75, a capacitor 76, a capacitor 77, and a sensor element 78. A wiring PR is electrically connected to a gate of the transistor 71. A wiring Tx is electrically connected to a gate of the transistor 72. A wiring W is electrically connected to a gate of the transistor 73. The wiring SE is electrically connected to a gate of the transistor 75. One of a source and a drain of the transistor 71 is electrically connected to one of a source and a drain of the transistor 72 and one electrode of the capacitor 76. The other of the source and the drain of the transistor 71 is electrically connected to the wiring 64. The other of the source and the drain of the transistor 72 is electrically connected to one electrode of the sensor element 78. The other electrode of the sensor element 78 is electrically connected to the wiring 65. The other electrode of the capacitor 76 is electrically connected to one of a source and a drain of the transistor 73, a gate of the transistor 74, and one electrode of the capacitor 77. The wiring 66 is electrically connected to the other of the source and the drain of the transistor 73 and the other electrode of the capacitor 77. One of a source and a drain of the transistor 74 is electrically connected to one of a source and a drain of the transistor 75. The other of the source and the drain of the transistor 74 is electrically connected to the wiring 67. The other of the source and the drain of the transistor 75 is electrically connected to the wiring S2.

An OS transistor including a metal oxide in a semiconductor layer can be used as each of the transistor 71 to the transistor 75. The OS transistor has a feature of an extremely low off-state current. When OS transistors are used as the transistor 71 to the transistor 75, a period during which charge can be retained in the capacitor 76 and the capacitor 77 can be elongated greatly.

Note that the transistor 74 may include a semiconductor layer different from those in the transistor 71 to the transistor 73 and the transistor 75. For example, the transistor 74 may be a Si transistor including Si in its semiconductor layer. When the transistor 74 is a Si transistor, responsiveness of the transistor can be improved. Moreover, when the transistor 75 is an OS transistor, owing to its low off-state current, leakage current to the wiring S2 can be inhibited. When the transistor 71 is an OS transistor, leakage current to the capacitor 76 can be reduced. When the transistor 73 is an OS transistor, a period during which charge can be retained in the capacitor 77 can be elongated greatly.

For another example, the transistor 74 may include a semiconductor layer different from those in the transistor 71 to the transistor 73 and the transistor 75. For example, the transistor 74 may be an OS transistor. In the case where the transistor 74 is an OS transistor, the channel length of the transistor can be reduced. When the transistor 71 to the transistor 73 and the transistor 75 are Si transistors, the channel lengths of the transistors can be reduced. That is, the resolution of the sensor region 41 can be increased.

[OS Transistor]

As a semiconductor material used for an OS transistor, a metal oxide whose energy gap is greater than or equal to 2 eV, preferably greater than or equal to 2.5 eV, further preferably greater than or equal to 3 eV can be used. A typical example is an oxide semiconductor containing indium, and a CAAC-OS or a CAC-OS described later can be used, for example. A CAAC-OS has a crystal structure including stable atoms and is suitable for a transistor that is required to have high reliability, and the like. A CAC-OS has high mobility and is suitable for a transistor that operates at high speed, and the like.

An OS transistor has a large energy gap of a semiconductor layer and thus exhibits extremely low off-state current characteristics. An OS transistor has the following features different from that of a Si transistor: impact ionization, an avalanche breakdown, a short-channel effect, or the like does not occur. Thus, the use of an OS transistor enables formation of a circuit having high withstand voltage and high reliability. Moreover, variations in electrical characteristics due to crystallinity unevenness, which are caused in Si transistors, are less likely to occur in OS transistors.

The semiconductor layer included in the OS transistor can be, for example, a film represented by an In-M-Zn-based oxide that contains indium, zinc, and M (a metal such as aluminum, titanium, gallium, germanium, yttrium, zirconium, lanthanum, cerium, tin, neodymium, or hafnium).

In the case where the oxide semiconductor contained in the semiconductor layer is an In-M-Zn-based oxide, it is preferable that the atomic ratio of metal elements in a sputtering target used for forming a film of the In-M-Zn oxide satisfy In M and Zn M. The atomic ratio of metal elements in such a sputtering target is preferably, for example, In:M:Zn=1:1:1, In:M:Zn=1:1:1.2, In:M:Zn=3:1:2, In:M:Zn=4:2:3, In:M:Zn=4:2:4.1, In:M:Zn=5:1:6, In:M:Zn=5:1:7, or In:M:Zn=5:1:8. Note that the atomic ratio in the formed semiconductor layer may vary from the above atomic ratio of metal elements in the sputtering target in a range of ±40%.

An oxide semiconductor with low carrier density is used for the semiconductor layer. For example, the semiconductor layer may use an oxide semiconductor whose carrier density is lower than or equal to $1\times10^{17}/cm^3$, preferably lower than or equal to $1\times10^{15}/cm^3$, further preferably lower than or equal to $1\times10^{13}/cm^3$, still further preferably lower than or equal to $1\times10^{11}/cm^3$, even further preferably lower than $1\times10^{10}/cm^3$, and higher than or equal to $1\times10^{-9}/cm^3$. Such an oxide semiconductor is referred to as a highly purified intrinsic or substantially highly purified intrinsic oxide semiconductor. The oxide semiconductor has a low density of defect states and can thus be regarded as having stable characteristics.

Note that, without limitation to these, a material with an appropriate composition may be used in accordance with required semiconductor characteristics and electrical characteristics (e.g., field-effect mobility and threshold voltage) of the transistor. To obtain the required semiconductor characteristics of the transistor, it is preferable that the carrier density, the impurity concentration, the defect density, the atomic ratio between a metal element and oxygen, the interatomic distance, the density, and the like of the semiconductor layer be set to appropriate values.

When the oxide semiconductor in the semiconductor layer contains silicon or carbon, which is an element belonging to Group 14, the amount of oxygen vacancies is increased, and the semiconductor layer becomes n-type. Thus, the concentration of silicon or carbon in the semiconductor layer (the concentration measured by secondary ion mass spectrometry) is set to $2\times10^{18}$ atoms/cm$^3$ or lower, preferably $2\times10^{17}$ atoms/cm$^3$ or lower.

An alkali metal and an alkaline earth metal might generate carriers when bonded to an oxide semiconductor, in which case the off-state current of the transistor might be increased. Therefore, the concentration of alkali metal or alkaline earth metal in the semiconductor layer (the concentration measured by secondary ion mass spectrometry) is set to $1\times10^{18}$ atoms/cm$^3$ or lower, preferably $2\times10^{16}$ atoms/cm$^3$ or lower.

When the oxide semiconductor in the semiconductor layer contains nitrogen, electrons functioning as carriers are generated and the carrier density increases, so that the semiconductor layer easily becomes n-type. Thus, a transistor using an oxide semiconductor that contains nitrogen is likely to be normally on. Hence, the concentration of nitrogen in the semiconductor layer (the concentration measured by secondary ion mass spectrometry) is preferably set to $5\times10^{18}$ atoms/cm$^3$ or lower.

The semiconductor layer may have a non-single-crystal structure, for example. Examples of a non-single-crystal structure include a CAAC-OS (C-axis Aligned Crystalline Oxide Semiconductor) including a c-axis aligned crystal, a polycrystalline structure, a microcrystalline structure, and an amorphous structure. Among the non-single-crystal structures, an amorphous structure has the highest density of defect states, whereas the CAAC-OS has the lowest density of defect states.

An oxide semiconductor film having an amorphous structure has disordered atomic arrangement and no crystalline component, for example. In another example, an oxide film having an amorphous structure has a completely amorphous structure and no crystal part.

Note that the semiconductor layer may be a mixed film including two or more of the following: a region having an amorphous structure, a region having a microcrystalline structure, a region having a polycrystalline structure, a region of CAAC-OS, and a region having a single crystal structure. The mixed film has, for example, a single-layer structure or a stacked-layer structure including two or more of the foregoing regions in some cases.

The composition of a CAC (Cloud-Aligned Composite)-OS, which is one embodiment of a non-single-crystal semiconductor layer, is described below.

The CAC-OS has, for example, a composition in which elements contained in an oxide semiconductor are unevenly distributed. Materials containing unevenly distributed elements each have a size of greater than or equal to 0.5 nm and less than or equal to 10 nm, preferably greater than or equal to 1 nm and less than or equal to 2 nm, or a similar size. Note that in the following description of an oxide semiconductor, a state in which one or more metal elements are unevenly distributed and regions containing the metal element(s) are mixed is referred to as a mosaic pattern or a patch-like pattern. The region has a size greater than or equal to 0.5 nm and less than or equal to 10 nm, preferably greater than or equal to 1 nm and less than or equal to 2 nm, or a similar size.

Note that an oxide semiconductor preferably contains at least indium. In particular, indium and zinc are preferably contained. In addition, one or more of aluminum, gallium, yttrium, copper, vanadium, beryllium, boron, silicon, titanium, iron, nickel, germanium, zirconium, molybdenum, lanthanum, cerium, neodymium, hafnium, tantalum, tungsten, magnesium, and the like may be contained.

For example, of the CAC-OS, an In—Ga—Zn oxide with the CAC composition (such an In—Ga—Zn oxide may be particularly referred to as CAC-IGZO) has a composition in which materials are separated into indium oxide (InO$_{X1}$, where X1 is a real number greater than 0) or indium zinc oxide (In$_{X2}$Zn$_{Y2}$O$_{Z2}$, where X2, Y2, and Z2 are real numbers greater than 0), and gallium oxide (GaO$_{X3}$, where X3 is a real number greater than 0) or gallium zinc oxide (Ga$_{X4}$Zn$_{Y4}$O$_{Z4}$, where X4, Y4, and Z4 are real numbers greater than 0), and a mosaic pattern is formed. Then, InO$_{X1}$ or In$_{X2}$Zn$_{Y2}$O$_{Z2}$ forming the mosaic pattern is evenly distributed in the film. This composition is also referred to as a cloud-like composition.

That is, the CAC-OS is a composite oxide semiconductor with a composition in which a region containing GaO$_{X3}$ as a main component and a region containing In$_{X2}$Zn$_{Y2}$O$_{Z2}$ or InO$_{X1}$ as a main component are mixed. Note that in this specification, when the atomic ratio of In to an element M in a first region is greater than the atomic ratio of In to an element M in a second region, for example, the first region is described as having higher In concentration than the second region.

Note that a compound containing In, Ga, Zn, and O is also known as IGZO. Typical examples of IGZO include a crystalline compound represented by $InGaO_3(ZnO)_{m1}$ (m1 is a natural number) and a crystalline compound represented by $In_{(1+x0)}Ga_{(1-x0)}O_3(ZnO)_{m0}$ ($-1 \leq x0 \leq 1$; m0 is a given number).

The above crystalline compounds have a single crystal structure, a polycrystalline structure, or a CAAC structure. Note that the CAAC structure is a crystal structure in which a plurality of IGZO nanocrystals have c-axis alignment and are connected in the a-b plane direction without alignment.

The CAC-OS relates to the material composition of an oxide semiconductor. In a material composition of a CAC-OS containing In, Ga, Zn, and O, nanoparticle regions containing Ga as a main component are observed in part of the CAC-OS and nanoparticle regions containing In as a main component are observed in part thereof. These nanoparticle regions are randomly dispersed to form a mosaic pattern. Thus, the crystal structure is a secondary element for the CAC-OS.

Note that in the CAC-OS, a layered structure including two or more films with different atomic ratios is not included. For example, a two-layer structure of a film containing In as a main component and a film containing Ga as a main component is not included.

A boundary between the region containing $GaO_{X3}$ as a main component and the region containing $In_{X2}Zn_{Y2}O_{Z2}$ or $InO_{X1}$ as a main component is not clearly observed in some cases.

In the case where one or more of aluminum, yttrium, copper, vanadium, beryllium, boron, silicon, titanium, iron, nickel, germanium, zirconium, molybdenum, lanthanum, cerium, neodymium, hafnium, tantalum, tungsten, magnesium, and the like are contained instead of gallium in a CAC-OS, nanoparticle regions containing the selected metal element(s) as a main component(s) are observed in part of the CAC-OS and nanoparticle regions containing In as a main component are observed in part of the CAC-OS, and these nanoparticle regions are randomly dispersed to form a mosaic pattern in the CAC-OS.

The CAC-OS can be formed by a sputtering method under a condition where a substrate is not heated intentionally, for example. In the case where the CAC-OS is formed by a sputtering method, one or more of an inert gas (typically, argon), an oxygen gas, and a nitrogen gas may be used as a deposition gas. The ratio of the flow rate of an oxygen gas to the total flow rate of the deposition gas in deposition is preferably as low as possible, and for example, the ratio of the flow rate of the oxygen gas is preferably higher than or equal to 0% and lower than 30%, further preferably higher than or equal to 0% and lower than or equal to 10%.

The CAC-OS is characterized in that a clear peak is not observed when measurement is conducted using a θ/2θ scan by an out-of-plane method, which is an X-ray diffraction (XRD) measurement method. That is, it is found by the XRD measurement that there are no alignment in the a-b plane direction and no alignment in the c-axis direction in the measured areas.

In an electron diffraction pattern of the CAC-OS that is obtained by irradiation with an electron beam with a probe diameter of 1 nm (also referred to as a nanometer-sized electron beam), a ring-like region (ring region) with high luminance and a plurality of bright spots in the ring region are observed. Thus, it is found from the electron diffraction pattern that the crystal structure of the CAC-OS includes a nanocrystalline (nc) structure that does not show alignment in the plane direction and the cross-sectional direction.

For example, energy dispersive X-ray spectroscopy (EDX) is used to obtain EDX mapping, and according to the EDX mapping, the CAC-OS of the In—Ga—Zn oxide has a composition in which the region containing $GaO_{X3}$ as a main component and the region containing $In_{X2}Zn_{Y2}O_{Z2}$ or $InO_{X1}$ as a main component are unevenly distributed and mixed.

The CAC-OS has a structure different from that of an IGZO compound in which metal elements are evenly distributed, and has characteristics different from those of the IGZO compound. That is, in the CAC-OS, the region containing $GaO_{X3}$ or the like as a main component and the region containing $In_{X2}Zn_{Y2}O_{Z2}$ or $InO_{X1}$ as a main component are separated to form a mosaic pattern.

The conductivity of the region containing $In_{X2}Zn_{Y2}O_{Z2}$ or $InO_{X1}$ as a main component is higher than that of the region containing $GaO_{X3}$ or the like as a main component. In other words, when carriers flow through the region containing $In_{X2}Zn_{Y2}O_{Z2}$ or $InO_{X1}$ as a main component, the conductivity of an oxide semiconductor is generated. Accordingly, when the regions containing $In_{X2}Zn_{Y2}O_{Z2}$ or $InO_{X1}$ as a main component are distributed like a cloud in an oxide semiconductor, high field-effect mobility (μ) can be achieved.

By contrast, the insulating property of the region containing $GaO_{X3}$ or the like as a main component is superior to that of the region containing $In_{X2}Zn_{Y2}O_{Z2}$ or $InO_{X1}$ as a main component. In other words, when the regions containing $GaO_{X3}$ or the like as a main component are distributed in an oxide semiconductor, leakage current can be suppressed and favorable switching operation can be achieved.

Accordingly, when a CAC-OS is used in a semiconductor element, the insulating property derived from $GaO_{X3}$ or the like and the conductivity derived from $In_{X2}Zn_{Y2}O_{Z2}$ or $InO_{X1}$ complement each other, whereby high on-state current ($I_{on}$) and high field-effect mobility (μ) can be achieved.

A semiconductor element using a CAC-OS has high reliability. Thus, the CAC-OS is suitably used as a material in a variety of semiconductor devices.

FIG. 4C1 is a circuit diagram illustrating the circuit 46. The circuit 46 includes a transistor 81, a terminal 83, and a terminal 84. A gate of the transistor 81 is electrically connected to a wiring BR. One of a source and a drain of the transistor 81 is electrically connected to the terminal 83 and the terminal 84. The other of the source and the drain of the transistor 81 is electrically connected to a wiring 68.

FIG. 4C2 is a circuit diagram illustrating a circuit 46a. The circuit 46a is different from FIG. 4C1 in that a transistor 82 is included. The wiring BR is electrically connected to the gate of the transistor 81 and a gate of the transistor 82. The wiring 68 is electrically connected to the other of the source and the drain of the transistor 81 and the other of the source and the drain of the transistor 82. The one of the source and the drain of the transistor 81 is electrically connected to the terminal 83 and the terminal 84.

Figure 5:
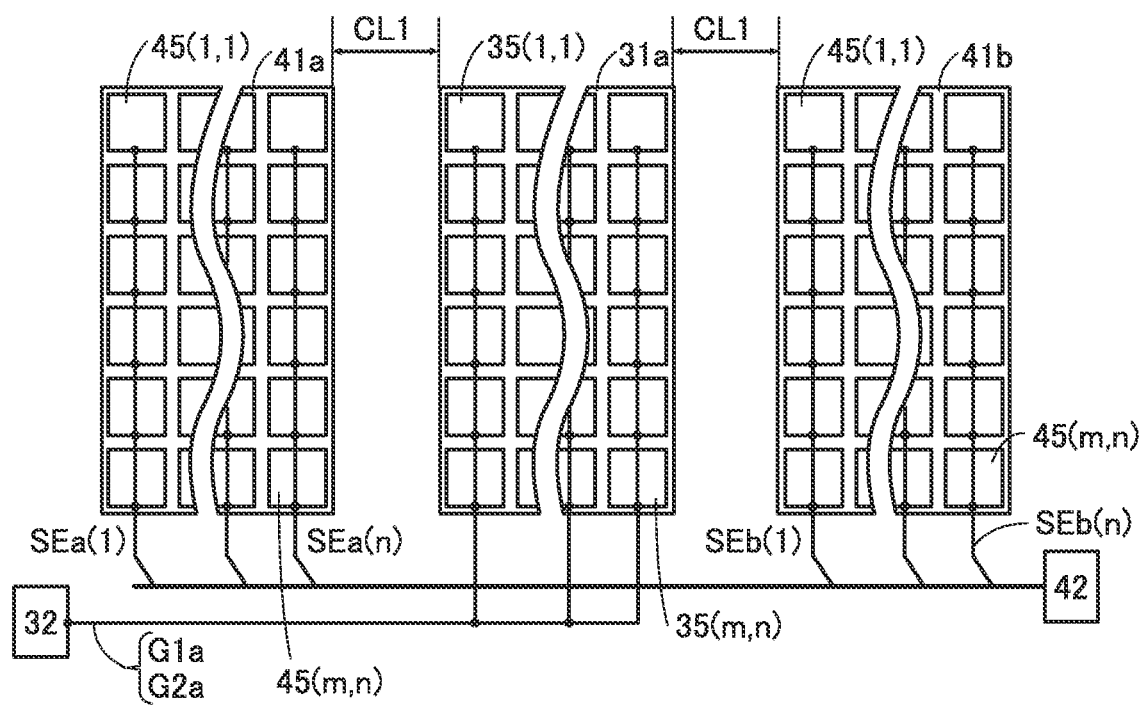
FIG. 5 is a diagram illustrating a sensor device.

FIG. 5 illustrates the sensor device 20a illustrated in FIG. 2, in detail. Note that FIG. 5 illustrates the light-emitting region 31a, the sensor region 41a, and the sensor region 41b for simplicity of description.

The sensor region 41a and the sensor region 41b are electrically connected to the circuit 42. The light-emitting region 31a is electrically connected to the circuit 32. The circuit 42 is electrically connected to the pixels 45 included in the sensor region 41a through a wiring SEa and the pixels 45 included in the sensor region 41b through a wiring SEb. The circuit 32 is electrically connected to the pixels 35 included in the light-emitting region 31a through a wiring G1a and a wiring G2a.

A region CL1 is formed between the sensor region 41a and the light-emitting region 31a, and a wiring, a circuit, or the like is not provided in the region CL1. A wiring, a circuit, or the like is not provided in the region CL1, whereby a distance between the sensor region 41a and the light-emitting region 31a is ensured. Thus, in the case where diffusion light emitted from the light-emitting region 31a is stray light, the stray light can be inhibited from entering the sensor region 41a when the region CL1 is ensured. Moreover, in the case where the sensor device 20a is flexible, a region in which a wiring, a circuit, or the like is not provided is included, so that there is no structure arranged in the region CL1 and the radius of curvature is small, improving flexibility.

Note that the pixel 45 including the sensor element may have the same size as or a different size from the pixel 35 including the light-emitting element 56. For example, in the case where the size of the pixel 45 is the same as the size of the pixel 35, the light-emitting region 31 and the sensor region 41 can use synchronized signals. Accordingly, the circuit structure can be simplified. The light-emitting region 31 and the sensor region 41 can be driven independently from each other. Thus, the sensor region 41 can be increased in size easily as compared to the light-emitting region 31.

An example in which the size of the pixel 45 is different from the size of the pixel 35 is described. In the case where concurrent lighting like light from a flash is performed in the light-emitting region 31, a time for supplying light emission data to a pixel can be reduced by increasing the size of the light-emitting element 56. The sensor region 41 can sense light reflected by an object by switching between a global shutter system and a rolling shutter system. For example, difference data between third sensing data and fourth sensing data sensed by the global shutter system can be sensed. The difference data is suitable for sensing the amount of change from the third sensing data obtained by sensing reflected light that changes when an object receives light to the fourth sensing data obtained by sensing reflected light from an object that changes over time.

The rolling shutter system is an operation method in which the plurality of pixels 45 included in the sensor region 41 perform exposure and data reading sequentially and a reading period of a row overlaps with an exposure period of another row. Note that exposure means to convert light received by a sensor element into a voltage by a photoelectric conversion function. The reading operation is performed right after the exposure, so that image capturing can be performed even with a circuit structure having a relatively short sensing data retention period. However, an image of one frame is formed with sensing data that do not have simultaneity of image capturing, and thus image distortion is generated in the captured image of a moving object.

In contrast, the global shutter system is an operation method in which exposure is performed on all the pixels at the same time, sensing data is retained in each pixel, and data reading is performed row by row. Thus, an image without distortion can be obtained even when an image of a moving object is captured.

For example, when a transistor using a metal oxide in a semiconductor layer is used as each of the transistor 73 and the transistor 75 included in the pixel 45, a period during which charge is retained in the capacitor 77 can be elongated greatly. Therefore, the global shutter system by which charge accumulation operation is performed in all the pixels at the same time can be used without complicating the circuit structure and the operation method.

Figure 6:
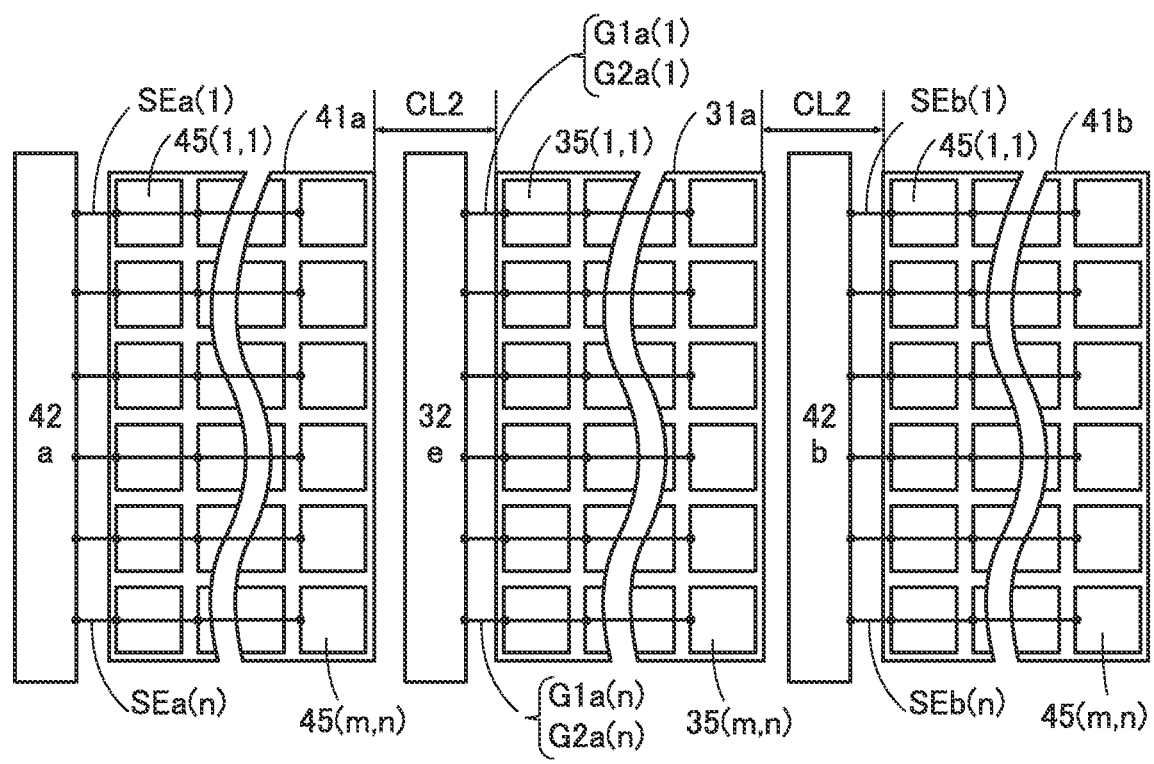
FIG. 6 is a diagram illustrating a sensor device.

FIG. 6 illustrates the sensor device 20a, which is different from that in FIG. 5, in detail. The light-emitting region 31a, the sensor region 41a, and the sensor region 41b are described.

The sensor region 41a, the light-emitting region 31a, and the sensor region 41b are electrically connected to a circuit 42a, a circuit 32e, and a circuit 42b, respectively. The circuit 42a is electrically connected to the pixels 45 included in the sensor region 41a through the wiring SEa. The circuit 32e is electrically connected to the pixels 35 included in the light-emitting region 31a through the wiring G1a and the wiring G2a. The circuit 42b is electrically connected to the pixels 45 included in the sensor region 41b through the wiring SEb.

A region CL2 is formed between the sensor region 41a and the light-emitting region 31a, and the circuit 32e is provided in the region CL2. In the case where diffusion light emitted from the light-emitting region 31a is stray light, the stray light is blocked by the circuit 32e arranged in the region CL2 and can be inhibited from entering the sensor region 41a.

Figure 7:
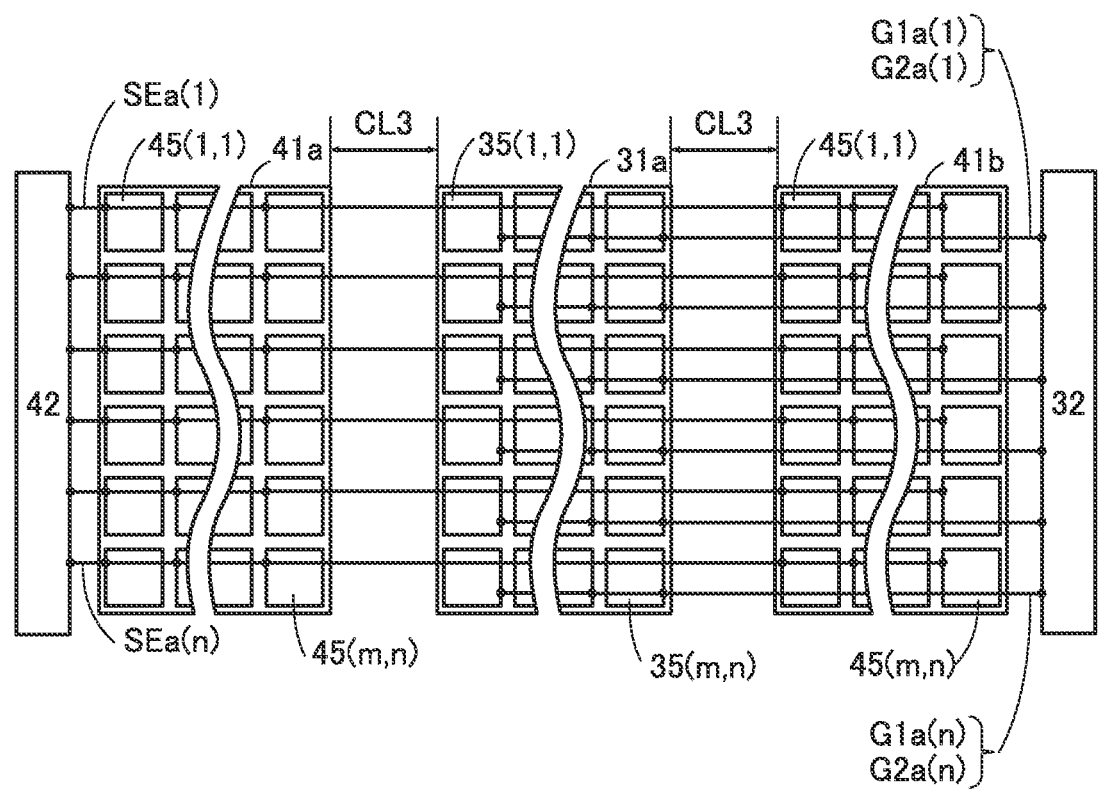
FIG. 7 is a diagram illustrating a sensor device.

FIG. 7 illustrates the sensor device 20a, which is different from that in FIG. 6, in detail. The light-emitting region 31a, the sensor region 41a, and the sensor region 41b are described.

The sensor region 41a and the sensor region 41b are electrically connected to the circuit 42. The light-emitting region 31a is electrically connected to the circuit 32. The circuit 42 is electrically connected to the pixels 45 included in the sensor region 41a and the sensor region 41b through the wiring SEa. The circuit 32 is electrically connected to the pixels 35 included in the light-emitting region 31a through the wiring G1a and the wiring G2a.

A region CL3 is formed between the sensor region 41a and the light-emitting region 31a, and the wiring is provided in the region CL3. A distance between the sensor region 41a and the light-emitting region 31a is ensured by the region CL3. Thus, in the case where diffusion light emitted from the light-emitting region 31a is stray light, the region CL3 can inhibit the stray light from entering the sensor region 41a. Moreover, in the case where the sensor device 20a is flexible, a region in which a circuit or the like is not provided is included, so that there is no structure arranged in the region CL3 and the radius of curvature is small, improving flexibility.

[Organic Light-Emitting Element]

An organic light-emitting element can be used as the light-emitting element 56. An element that emits infrared light can be used as the organic light-emitting element. In particular, the organic light-emitting element preferably emits infrared light having a peak at a wavelength greater than or equal to 700 nm and less than or equal to 9000 nm.

When an organic light-emitting element is used as the light-emitting element 56, an imaging device with a thin light source can be achieved. The imaging device can easily be incorporated in various devices and the portability can be improved.

As the organic light-emitting element, a light-emitting element (EL element) that utilizes electroluminescence can be used. An EL element includes a layer containing a light-emitting compound (EL layer) between a pair of electrodes. By generating a potential difference between the pair of electrodes that is greater than the threshold voltage of the EL element, holes are injected into the EL layer from the anode side and electrons are injected into the EL layer from the cathode side. The injected electrons and holes are recombined in the EL layer and the light-emitting substance contained in the EL layer emits light.

EL elements are classified depending on whether a light-emitting material is an organic compound or an inorganic compound; in general, the former is referred to as an organic EL element, and the latter is referred to as an inorganic EL element.

In an organic EL element, voltage application causes electrons to be injected from one electrode to the EL layer and holes to be injected from the other electrode to the EL layer. Then, the carriers (electrons and holes) recombine, so that the light-emitting organic compound forms an excited state, and light is emitted when the excited state returns to a ground state. Owing to such a mechanism, this light-emitting element is referred to as a current-excitation light-emitting element.

The EL layer can be formed by a method such as an evaporation method (including a vacuum evaporation method), a transfer method, a printing method, an inkjet method, or a coating method.

Inorganic EL elements are classified according to their element structures into a dispersion-type inorganic EL element and a thin-film inorganic EL element. A dispersion-type inorganic EL element includes a light-emitting layer where particles of a light-emitting material are dispersed in a binder, and its light emission mechanism is donor-acceptor recombination type light emission that utilizes a donor level and an acceptor level. A thin-film inorganic EL element has a structure where a light-emitting layer is sandwiched between dielectric layers, which are further sandwiched between electrodes, and its light emission mechanism is localization type light emission that utilizes inner-shell electron transition of metal ions.

A structure of the light-emitting element will be described. For example, the EL layer can include a plurality of layers such as a first layer, a light-emitting layer, and a second layer. The first layer can include a layer containing a substance having a high electron-injection property (electron-injection layer), a layer containing a substance having a high electron-transport property (electron-transport layer), and the like, for example. The light-emitting layer contains a light-emitting compound, for example. The second layer can include a layer containing a substance having a high hole-injection property (hole-injection layer) and a layer containing a substance having a high hole-transport property (hole-transport layer), for example.

The EL layer provided between a first electrode and a second electrode can function as a single light-emitting unit. Note that a plurality of light-emitting layers may be provided between the first layer and the second layer. Note that a light-transmitting conductive film is used as either of the first electrode and the second electrode, whereby the light emission direction is determined.

The light-emitting element can emit light of various wavelengths depending on the material of the EL layer. In one embodiment of the present invention, a material that emits infrared light (light having a peak wavelength from 700 nm to 9000 nm) is used as a material of the EL layer. For example, a material that emits light having a peak wavelength in a target wavelength range, such as at 720 nm, 760 nm, 850 nm, or 900 nm, is used as appropriate in accordance with the uses.

Note that in one embodiment of the present invention, it is preferable that the EL layer include an organometallic iridium complex that emits infrared light as the light-emitting material (also referred to as a guest material or a dopant material). The organometallic iridium complex preferably includes a dimethylphenyl skeleton and a quinoxaline skeleton. Furthermore, as the organometallic iridium complex, bis{4,6-dimethyl-2-[3-(3,5-dimethylphenyl)-2-quinoxalinyl-κN]phenyl-κC}(2,2',6,6'-tetramethyl-3,5-heptanedionato-κ$^2$O,O')iridium(III) (abbreviation: Ir(dmdpq)$_2$(dpm)) or the like can be typically used. With the use of the above-described organometallic iridium complex, it is possible to provide an imaging element with high quantum efficiency or high emission efficiency.

As the substance (i.e., a host material) used for dispersing the organometallic iridium complex, it is preferable to use a compound having an arylamine skeleton such as 2,3-bis(4-diphenylaminophenyl)quinoxaline (abbreviation: TPAQn) or NPB, a carbazole derivative such as CBP or 4,4',4"-tris(carbazol-9-yl)triphenylamine (abbreviation: TCTA), or a metal complex such as bis[2-(2-hydroxyphenyl)pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolato)(4-phenyphenolato)aluminum (abbreviation: BAlq), or tris(8-quinolinolato)aluminum (abbreviation: Alq$_3$), for example. In addition, a high molecular compound such as PVK can be used.

As the material (host material) used for dispersing the organometallic iridium complex, N-(1,1'-biphenyl-4-yl)-N-[4-(9-phenyl-9H-carbazol-3-yl)phenyl]-9,9-dimethyl-9H-fluoren-2-amine (abbreviation: PCBBiF) is suitably used.

Note that when the light-emitting layer is formed so as to contain the above-described organometallic iridium complex (guest material) and the above-described host material, infrared phosphorescence can be obtained from the EL layer with high emission efficiency.

At least part of this embodiment can be implemented in combination with the other embodiments described in this specification as appropriate.

Embodiment 2

In this embodiment, a sensor device of one embodiment of the present invention will be described with reference to FIG. 8 to FIG. 15.

The sensor device described below as an example is a device having a light-emitting function and an imaging function. The sensor device described below as an example can be used in the light-emitting region or the sensor region in Embodiment 1.

[Overview]

The sensor device of this embodiment includes a sensor element and a light-emitting element over a flexible substrate. Specifically, light-emitting elements are arranged in matrix in a light-emitting region and the light-emitting region functions as a light source. Sensor elements are arranged in matrix in the sensor region and the sensor region functions as a light-receiving portion. The light-receiving portion can be used for an inspection sensor, an image sensor, or a touch sensor. That is, by sensing light with the light-receiving portion, reflected light from an object that has received light from the light-emitting element can be sensed, or the approach or contact of an object (e.g., a finger or a stylus) can be sensed.

In the sensor device of one embodiment of the present invention, when light emitted from the light-emitting element included in the light-emitting region is reflected by an object, the sensor element in the sensor region can sense the reflected light; thus, the sensor device can be used by being attached to an object or can be easily incorporated in a wearable electronic device (e.g., a watch).

The light-emitting element may be an organic light-emitting element. For example, as the organic light-emitting element, an EL element such as an OLED (Organic Light Emitting Diode) or a QLED (Quantum-dot Light Emitting Diode) can be used. As a light-emitting substance included in the EL element, a substance emitting fluorescence (fluorescent material), a substance emitting phosphorescence (phosphorescent material), an inorganic compound (e.g., quantum dot material), and a substance exhibiting thermally activated delayed fluorescence (Thermally activated delayed fluorescence (TADF) material) can be given as examples. Alternatively, a light-emitting diode (LED) such as a micro-LED can be used as the light-emitting element by being bonded to a pixel. The light-emitting element includes an organic light-emitting element (EL element), a micro-LED, and the like in the following description.

The sensor device of this embodiment has a function of sensing light with the use of the sensor element.

The sensor element is preferably capable of sensing light having a peak wavelength of 700 nm or greater. By sensing light of 700 nm or greater that returns as reflected light from an object, a kind, composition, an image, and the like of the object can be sensed.

For example, hemoglobin, glucose, or the like in the blood can be sensed with the sensor device. Furthermore, the sugar content of fruit, a foreign substance such as a needle mixed in clothes, or the like can be sensed. That is, the sensor device of this embodiment can provide a physiological monitor or a biometric authentication sensor. For example, when the sensor device is incorporated in an electronic device such as a watch, the number of components of the electronic device can be reduced as compared to the case where a physiological monitor is provided separately from the sensor device, and the size and the weight of the electronic device can be reduced.

In the case where the sensor element is used for a touch sensor, the sensor device of this embodiment can function as a sensor for biometric authentication such as vein authentication using the sensor element.

As the sensor element, a pn or pin photodiode can be used, for example. The sensor element functions as a photoelectric conversion element that senses light entering the sensor element and generates charge. The amount of generated charge depends on the amount of incident light.

It is particularly preferable to use an organic photodiode including a layer containing an organic compound as the sensor element. An organic photodiode, which is easily made thin, lightweight, and large in area and has a high degree of freedom for shape and design, can be used in a variety of sensor devices.

In one embodiment of the present invention, an organic EL element is used as the light-emitting element and an organic photodiode is used as the sensor element. A plurality of layers can be shared by the organic photodiode and the organic EL element. Therefore, the sensor element can be incorporated in the sensor device without a significant increase in the number of manufacturing steps. For example, it is possible that an active layer of the sensor element and a light-emitting layer of the light-emitting element are separately formed and other layers are shared by the light-emitting element and the sensor element.

Figure 8A:
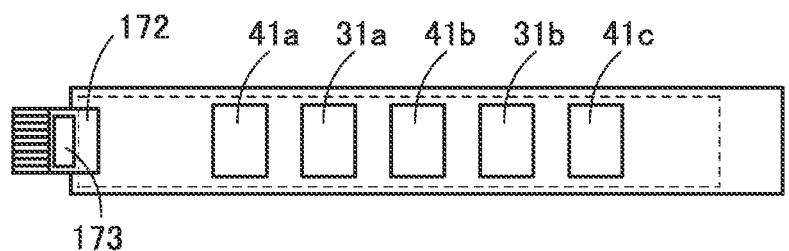
FIG. 8A and FIG. 8B are diagrams illustrating sensor devices.
Figure 8B:
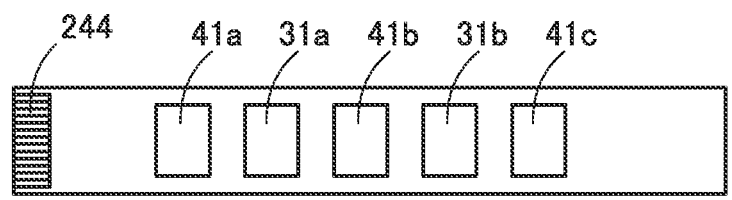

FIG. 8A and FIG. 8B illustrate sensor devices of embodiments of the present invention.

A sensor device 100A illustrated in FIG. 8A includes the light-emitting regions (31a, 31b), the sensor regions (41a, 41b, 41c), and an FPC 172. The sensor device 100A is electrically connected to a semiconductor device through the FPC 172. Note that an IC (integrated circuit) including an image processing circuit may be provided over the FPC 172 by a COG (Chip On Glass) method, a COF (Chip on Film) method, or the like. For example, an IC 173 preferably includes a timing control circuit, a signal line driver circuit, a source follower circuit, an analog/digital converter circuit, or the like. Note that as the IC 173, a packaged IC may be mounted using an anisotropic conductive film (ACF) or an anisotropic conductive paste (ACP), or a bare chip may be mounted by a flip-chip mounting method.

The sensor device illustrated in FIG. 8B can be connected to a semiconductor device not through the FPC 172 but through an electrode 244 provided over a substrate. Note that FIG. 8B illustrates a structure in which an IC is not provided in the sensor device 100A as an example.

Note that in FIG. 8A or FIG. 8B, a layer including a sensor element transistor, a layer including a sensor element, and a layer including a light-emitting element are provided between a first substrate and a second substrate.

The detailed structure of the sensor device of one embodiment of the present invention is described below with reference to FIG. 9 to FIG. 11.

[Sensor Device 300A]

Figure 9A:
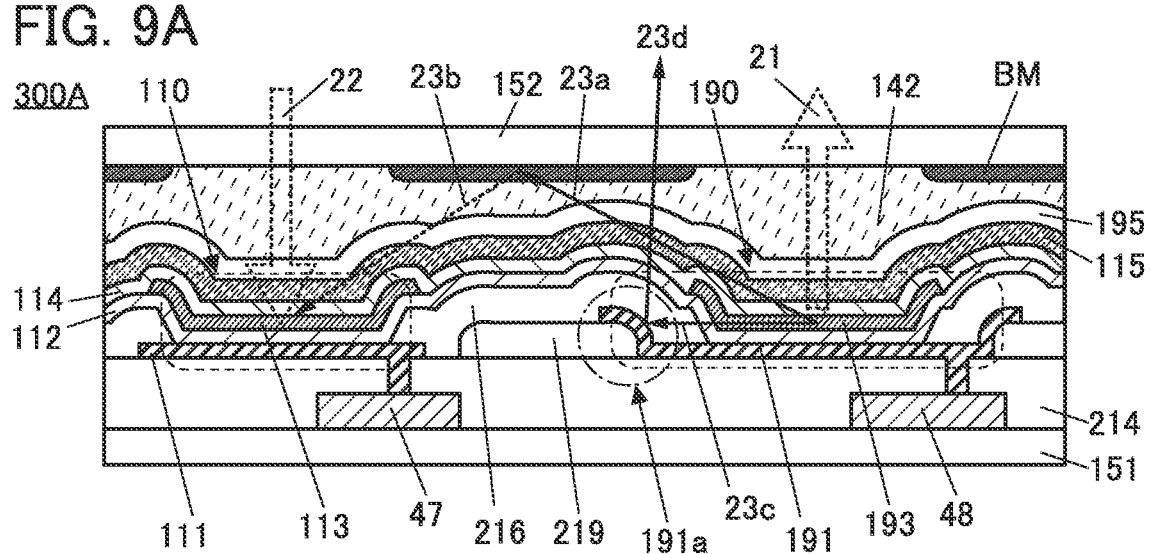
FIG. 9A to FIG. 9C are cross-sectional views each illustrating an example of a sensor device.

FIG. 9A is a cross-sectional view of a sensor device 300A.

The sensor device 300A includes a sensor element 110 and a light-emitting element 190.

The sensor element 110 includes a pixel electrode 111, a common layer 112, an active layer 113, a common layer 114, and a common electrode 115.

The light-emitting element 190 includes a pixel electrode 191, the common layer 112, a light-emitting layer 193, the common layer 114, and the common electrode 115.

The pixel electrode 111, the pixel electrode 191, the common layer 112, the active layer 113, the light-emitting layer 193, the common layer 114, and the common electrode 115 may each have a single-layer structure or a stacked-layer structure.

A partition wall 219 is positioned over an insulating layer 214. The partition wall 219 is an insulating layer.

The pixel electrode 111 and the pixel electrode 191 are positioned over the insulating layer 214. Note that the pixel electrode 191 is positioned over the insulating layer 214 and the partition wall 219. The pixel electrode 111 and the pixel electrode 191 can be formed using the same material in the same step.

The common layer 112 is positioned over the pixel electrode 111 and the pixel electrode 191. The common layer 112 is shared by the sensor element 110 and the light-emitting element 190.

The active layer 113 overlaps with the pixel electrode 111 with the common layer 112 therebetween. The light-emitting layer 193 overlaps with the pixel electrode 191 with the common layer 112 therebetween. The active layer 113 contains a first organic compound, and the light-emitting layer 193 contains a second organic compound that is different from the first organic compound.

The common layer 114 is positioned over the common layer 112, the active layer 113, and the light-emitting layer 193. The common layer 114 is shared by the sensor element 110 and the light-emitting element 190.

The common electrode 115 includes a portion overlapping with the pixel electrode 111 with the common layer 112, the active layer 113, and the common layer 114 therebetween. The common electrode 115 further includes a portion overlapping with the pixel electrode 191 with the common layer 112, the light-emitting layer 193, and the common layer 114 therebetween. The common electrode 115 is shared by the sensor element 110 and the light-emitting element 190.

In the sensor device of this embodiment, an organic compound is used for the active layer 113 of the sensor element 110. In the sensor element 110, the layers other than the active layer 113 can be common to the layers in the light-emitting element 190 (the EL element). Therefore, the sensor element 110 can be formed concurrently with the formation of the light-emitting element 190 only by adding a step of depositing the active layer 113 in the manufacturing process of the light-emitting element 190. The light-emitting element 190 and the sensor element 110 can be formed over the same substrate. Accordingly, the sensor element 110 can be incorporated into the sensor device without a significant increase in the number of manufacturing steps.

The sensor device 300A shows an example in which the sensor element 110 and the light-emitting element 190 have a common structure except that the active layer 113 of the sensor element 110 and the light-emitting layer 193 of the light-emitting element 190 are separately formed. Note that the structures of the sensor element 110 and the light-emitting element 190 are not limited thereto. The sensor element 110 and the light-emitting element 190 may include separately formed layers other than the active layer 113 and the light-emitting layer 193 (see sensor devices 300K, 300L, and 300M described later). The sensor element 110 and the light-emitting element 190 preferably include at least one layer used in common (common layer). Thus, the sensor element 110 can be incorporated into the sensor device without a significant increase in the number of manufacturing steps.

The sensor device 300A includes the sensor element 110, the light-emitting element 190, a transistor 47, a transistor 48, and the like between a pair of substrates (a substrate 151 and a substrate 152).

In the sensor element 110, the common layer 112, the active layer 113, and the common layer 114 that are positioned between the pixel electrode 111 and the common electrode 115 can each be referred to as an organic layer (a layer containing an organic compound). The pixel electrode 111 preferably has a function of reflecting light. A partition wall 216 is positioned over the partition wall 219. End portions of the pixel electrode 111 are covered with the partition wall 216. The pixel electrode 111 included in the light-emitting element 190 includes a region 191a indicated by a dashed-dotted line, in which the partition wall 219 and the partition wall 216 are in contact with each other. The common electrode 115 has a function of transmitting light.

The sensor element 110 has a function of sensing light. Specifically, the sensor element 110 is a photoelectric conversion element that receives light 22 entering from the outside of the sensor device 300A and converts the light 22 into an electric signal. The light 22 can also be expressed as light that is emitted from the light-emitting element 190 and then reflected by an object. The light 22 may enter the sensor element 110 through a lens described later.

A light-blocking layer BM is provided on a surface of the substrate 152 on the substrate 151 side. The light-blocking layer BM has openings at a position overlapping with the sensor element 110 and at a position overlapping with the light-emitting element 190. Providing the light-blocking layer BM can control a range where light is sensed by the sensor element 110.

For the light-blocking layer BM, a material that blocks light emitted from the light-emitting element can be used. The light-blocking layer BM preferably absorbs light. As the light-blocking layer BM, a black matrix can be formed using a metal material or a resin material containing pigment (e.g., carbon black) or dye, for example. The light-blocking layer BM may have a stacked-layer structure of a red color filter, a green color filter, and a blue color filter.

Here, the sensor element 110 senses light that is emitted from the light-emitting element 190 and then reflected by an object. However, in some cases, light emitted from the light-emitting element 190 is reflected inside the sensor device 300A and enters the sensor element 110 without through an object. The light-blocking layer BM can inhibit the influence of such diffusion light. For example, in the case where the light-blocking layer BM is not provided, light 23a emitted from the light-emitting element 190 is reflected by the substrate 152, and reflected light 23b enters the sensor element 110 in some cases. Providing the light-blocking layer BM can inhibit entry of the reflected light 23b into the sensor element 110. Furthermore, with the region 191a, light 23c emitted from the light-emitting element 190 is reflected by the pixel electrode 191 and reflected light 23d is emitted in substantially the same direction as emitted light 21. Thus, light that might be diffusion light to be noise can be effectively used. That is, the pixel electrode 191 including the region 191a can have a light-blocking function and a light-collecting function. Thus, noise can be reduced and the sensitivity of the sensor using the sensor element 110 can be increased.

In the light-emitting element 190, the common layer 112, the light-emitting layer 193, and the common layer 114 that are positioned between the pixel electrode 191 and the common electrode 115 can each be referred to as an EL layer. The pixel electrode 191 preferably has a function of reflecting light. End portions of the pixel electrode 191 are covered with the partition wall 216. The pixel electrode 111 and the pixel electrode 191 are electrically insulated from each other by the partition wall 216. The common electrode 115 has a function of transmitting light.

The light-emitting element 190 has a function of emitting light. Specifically, the light-emitting element 190 is an electroluminescent element that emits light to the substrate 152 side (see the emitted light 21) by applying voltage between the pixel electrode 191 and the common electrode 115.

It is preferable that the light-emitting layer 193 be formed not to overlap with a light-receiving region (sensor region) of the sensor element 110. Accordingly, it is possible to inhibit the light-emitting layer 193 from absorbing the light 22, so that the amount of light with which the sensor element 110 is irradiated can be increased.

The pixel electrode 111 is electrically connected to a source or a drain included in the transistor 47 through an opening provided in the insulating layer 214. End portions of the pixel electrode 111 are covered with the partition wall 216.

The pixel electrode 191 is electrically connected to a source or a drain included in the transistor 48 through an opening provided in the insulating layer 214. End portions of the pixel electrode 191 are covered with the partition wall 216. The transistor 48 has a function of controlling the driving of the light-emitting element 190.

The transistor 47 and the transistor 48 are on and in contact with the same layer (the substrate 151 in FIG. 9A).

At least part of a circuit electrically connected to the sensor element 110 is preferably formed using the same material in the same step as a circuit electrically connected to the light-emitting element 190. Accordingly, the thickness of the sensor device can be smaller than that in the case where the two circuits are separately formed, and the manufacturing process can be simplified.

The sensor element 110 and the light-emitting element 190 are preferably covered with a protective layer 195. In FIG. 9A, the protective layer 195 is provided on and in contact with the common electrode 115. With the protective layer 195, entry of impurities such as water into the sensor element 110 and the light-emitting element 190 can be inhibited, leading to an increase in the reliability of the sensor element 110 and the light-emitting element 190. The protective layer 195 and the substrate 152 are bonded to each other with an adhesive layer 142.

Figure 10A:
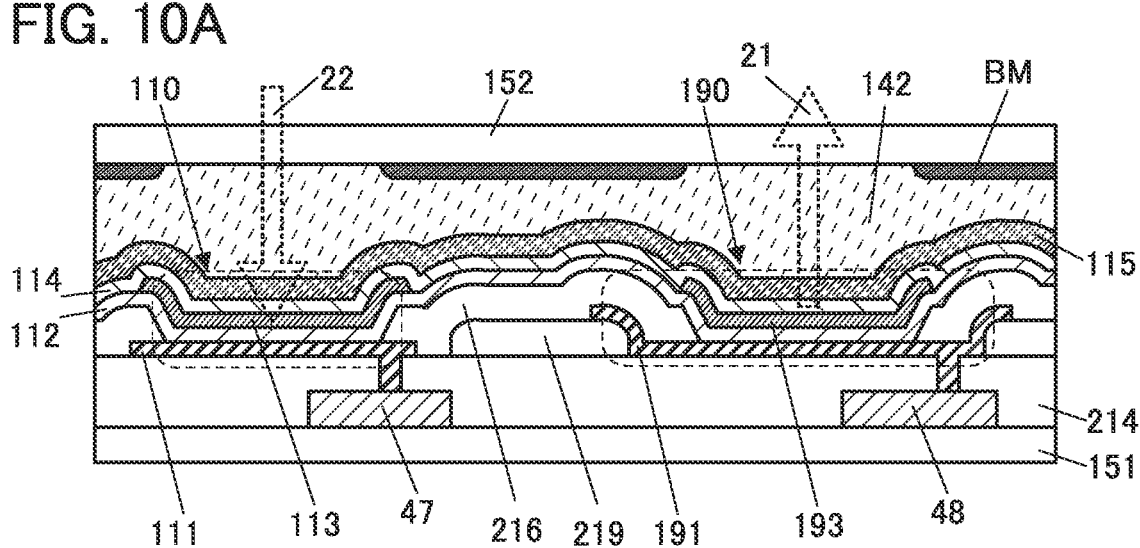
FIG. 10A to FIG. 10C are cross-sectional views each illustrating an example of a sensor device.

Note that as shown in FIG. 10A, the protective layer is not necessarily provided over the sensor element 110 and the light-emitting element 190. In FIG. 10A, the common electrode 115 and the substrate 152 are bonded to each other with the adhesive layer 142.

[Sensor Device 300B]

Figure 9B:
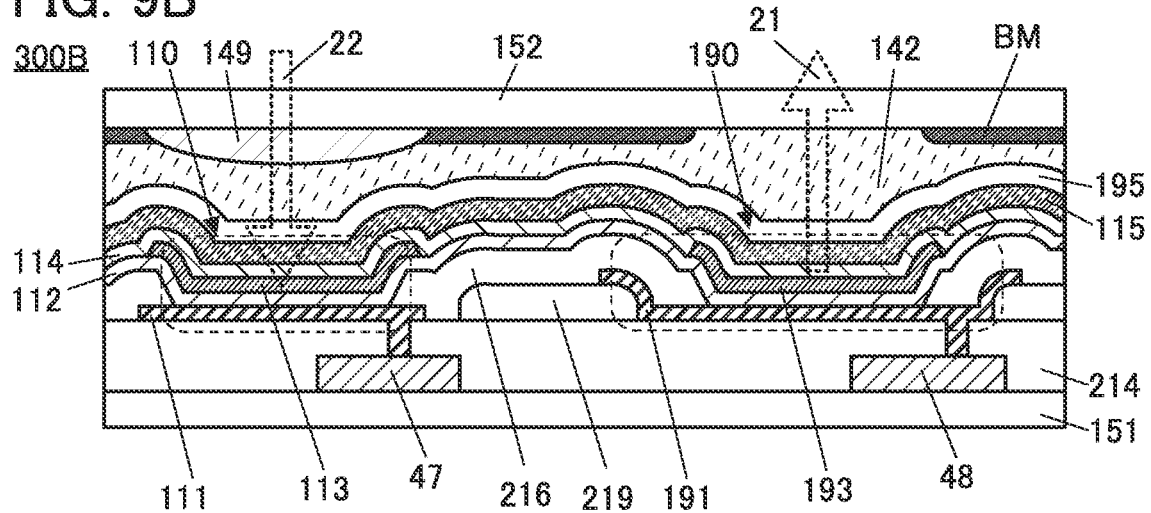

FIG. 9B is a cross-sectional view of a sensor device 300B. Note that in the following description of sensor devices, components similar to those of the above sensor device are not described in some cases.

The sensor device 300B illustrated in FIG. 9B includes a lens 149 in addition to the components of the sensor device 300A.

The sensor device of this embodiment may include the lens 149. The lens 149 is provided at a position overlapping with the sensor element 110. In the sensor device 300B, the lens 149 is provided in contact with the substrate 152. The lens 149 included in the sensor device 300B has a convex surface facing the substrate 151. Alternatively, the lens 149 may have a convex surface facing the substrate 152.

In the case where both the light-blocking layer BM and the lens 149 are formed on the same surface of the substrate 152, their formation order is not limited. Although FIG. 9B shows an example in which the lens 149 is formed first, the light-blocking layer BM may be formed first. In FIG. 9B, end portions of the lens 149 are covered with the light-blocking layer BM.

The sensor device 300B has a structure in which the light 22 enters the sensor element 110 through the lens 149. With the lens 149, the imaging range of the sensor element 110 can be narrowed as compared to the case where the lens 149 is not provided, thereby inhibiting overlap between the imaging ranges of the adjacent sensor elements 110. Thus, a clear image with little blurring can be captured. In the case where the imaging range of the sensor element 110 is the same, the lens 149 allows the size of a pinhole (corresponding to the size of an opening in the BM that overlaps with the sensor element 110 in FIG. 9B) to be increased, as compared to the case where the lens 149 is not provided. Hence, providing the lens 149 can increase the amount of light entering the sensor element 110.

Figure 10B:
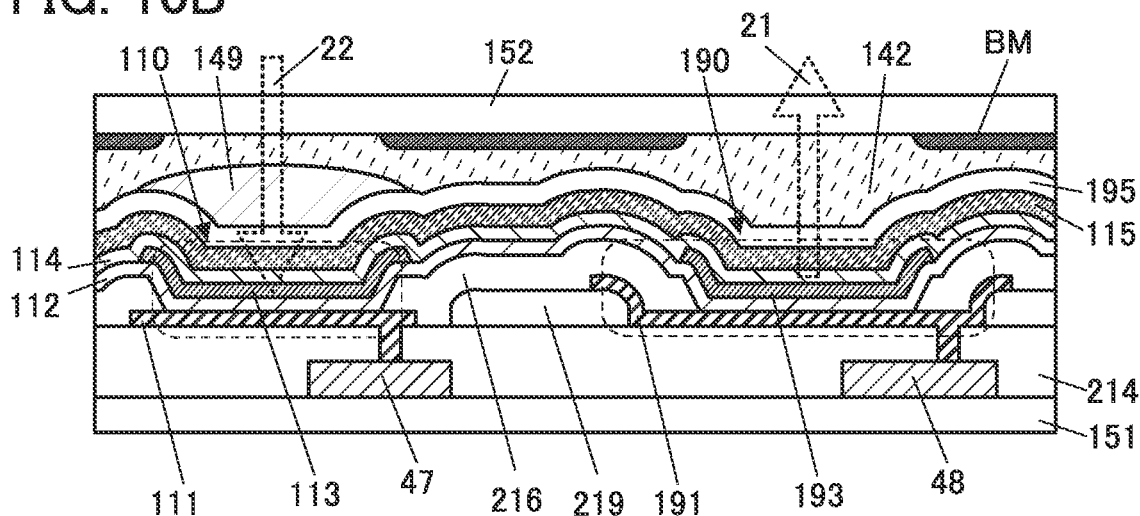
Figure 10C:
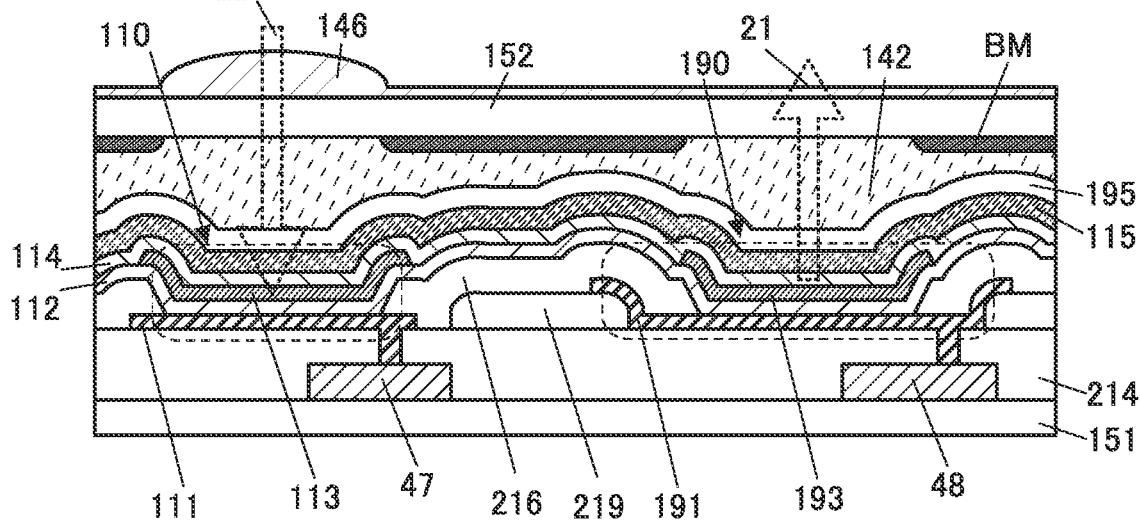

Like the sensor device 300B illustrated in FIG. 9B, each of sensor devices illustrated in FIG. 10B and FIG. 10C has a structure in which the light 22 enters the sensor element 110 through the lens 149.

In FIG. 10B, the lens 149 is provided in contact with a top surface of the protective layer 195. The lens 149 included in the sensor device illustrated in FIG. 10B has a convex surface facing the substrate 152.

In the sensor device illustrated in FIG. 10C, a lens array 146 is provided on a display surface side of the substrate 152. A lens included in the lens array 146 is provided at a position overlapping with the sensor element 110. The light-blocking layer BM is preferably provided on a surface of the substrate 152 on the substrate 151 side.

As a method for forming the lens used in the sensor device of this embodiment, a lens such as a microlens may be formed directly over the substrate or the sensor element, or a lens array manufactured separately, such as a microlens array, may be bonded to the substrate.

[Sensor Device 300C]

Figure 9C:
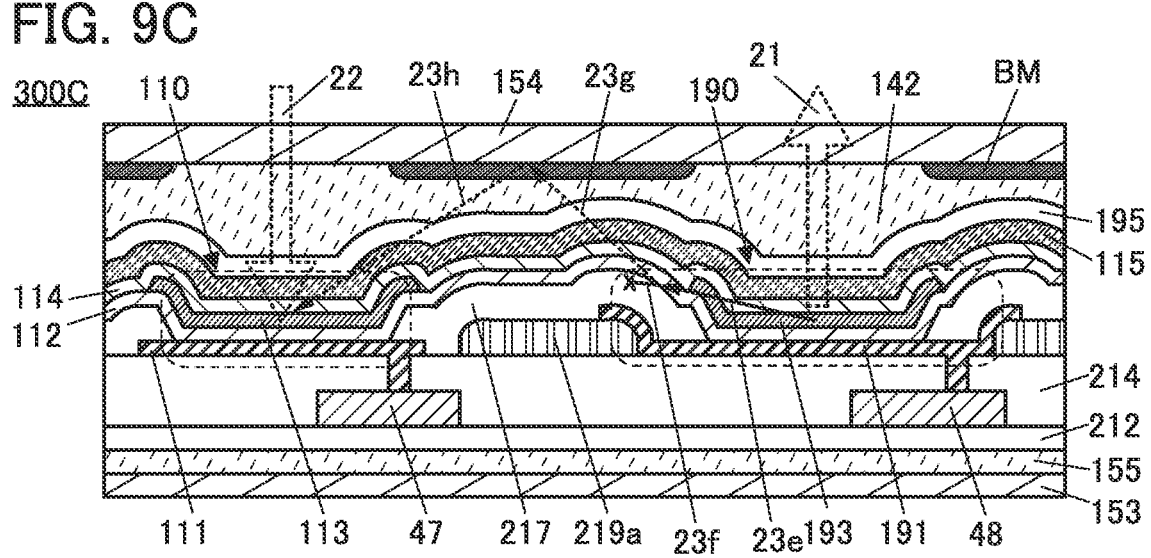

FIG. 9C is a cross-sectional view of a sensor device 300C.

The sensor device 300C illustrated in FIG. 9C is different from the sensor device 300A in that the substrate 151, the substrate 152, and the partition wall 216 are not included and a substrate 153, a substrate 154, an adhesive layer 155, an insulating layer 212, a partition wall 219a, and a partition wall 217 are included. Note that the partition wall 219a may be formed of an organic layer or a conductive layer.

The substrate 153 and the insulating layer 212 are bonded to each other with the adhesive layer 155. The substrate 154 and the protective layer 195 are bonded to each other with the adhesive layer 142.

The sensor device 300C is formed in such a manner that the insulating layer 212, the transistor 47, the transistor 48, the sensor element 110, the light-emitting element 190, and the like that are formed over a formation substrate are transferred onto the substrate 153. The substrate 153 and the substrate 154 are preferably flexible. Accordingly, the flexibility of the sensor device 300C can be increased. For example, a resin is preferably used for each of the substrate 153 and the substrate 154.

For each of the substrate 153 and the substrate 154, a polyester resin such as polyethylene terephthalate (PET) or polyethylene naphthalate (PEN), a polyacrylonitrile resin, an acrylic resin, a polyimide resin, a polymethyl methacrylate resin, a polycarbonate (PC) resin, a polyether sulfone (PES) resin, a polyamide resin (e.g., nylon or aramid), a polysiloxane resin, a cycloolefin resin, a polystyrene resin, a polyamide-imide resin, a polyurethane resin, a polyvinyl chloride resin, a polyvinylidene chloride resin, a polypropylene resin, a polytetrafluoroethylene (PTFE) resin, an ABS resin, or cellulose nanofiber can be used, for example. Glass that is thin enough to have flexibility may be used for one or both of the substrate 153 and the substrate 154.

As the substrate included in the sensor device of this embodiment, a film having high optical isotropy may be used. Examples of the film having high optical isotropy include a triacetyl cellulose (TAC, also referred to as cellulose triacetate) film, a cycloolefin polymer (COP) film, a cycloolefin copolymer (COC) film, and an acrylic film.

The partition wall 217 preferably absorbs light emitted from the light-emitting element. As the partition wall 217, a black matrix can be formed using a resin material containing a pigment or dye, for example. Moreover, the partition wall 217 can be formed of a colored insulating layer by using a brown resist material.

Light 23e emitted from the light-emitting element 190 is reflected by part of a surface of the partition wall 217 to be reflected light 23g. Part of the reflected light 23g is reflected by the substrate 154, and the reflected light 23h enters the sensor element 110 in some cases. In other cases, the light 23e passes through the partition wall 217 and is reflected by a transistor, a wiring, or the like, and thus reflected light enters the sensor element 110. In addition, part of light 23f is absorbed by the partition wall 217, whereby the amount of the reflected light 23g can be reduced and the amount of light entering the sensor element 110 can be suppressed. Thus, noise can be reduced and the sensitivity of the sensor using the sensor element 110 can be increased.

Accordingly, the partition wall 217 preferably absorbs at least light having a wavelength that is sensed by the sensor element 110. For example, in the case where the sensor element 110 senses green light emitted from the light-emitting element 190, the partition wall 217 preferably absorbs at least green light. For example, when the partition wall 217 includes a red color filter, the green light 23e can be absorbed, and thus the amount of the reflected light 23h entering the sensor element 110 can be suppressed.

[Sensor Devices 300K, 300L, 300M]

Figure 11A:
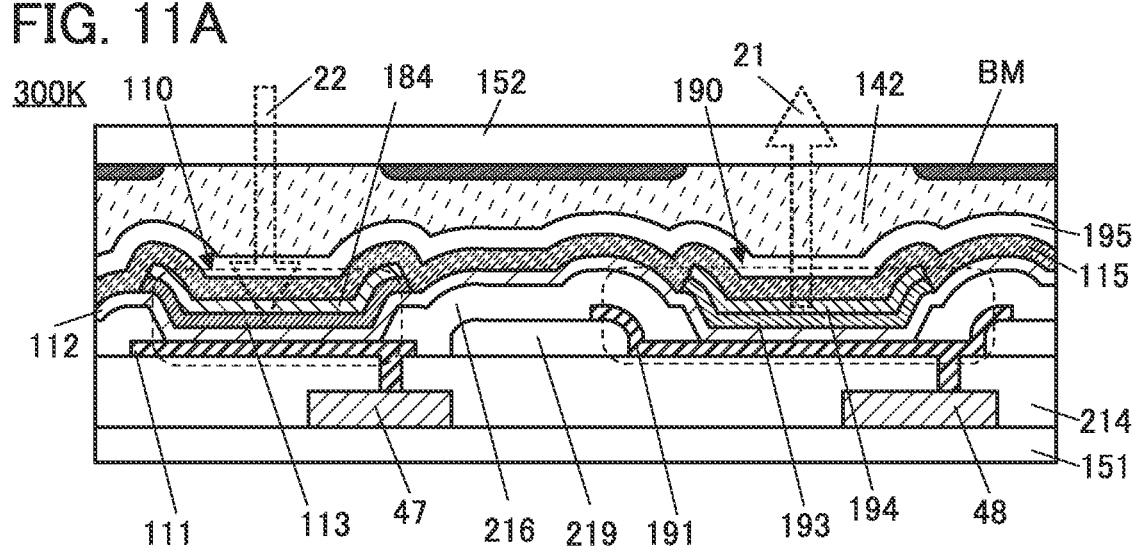
FIG. 11A to FIG. 11C are cross-sectional views each illustrating an example of a sensor device.
Figure 11B:
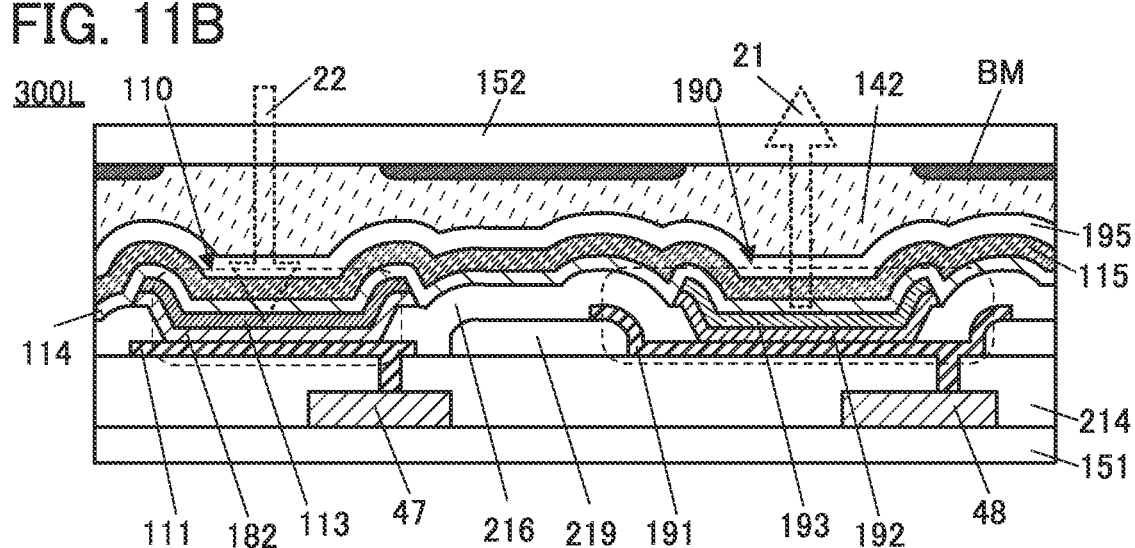
Figure 11C:
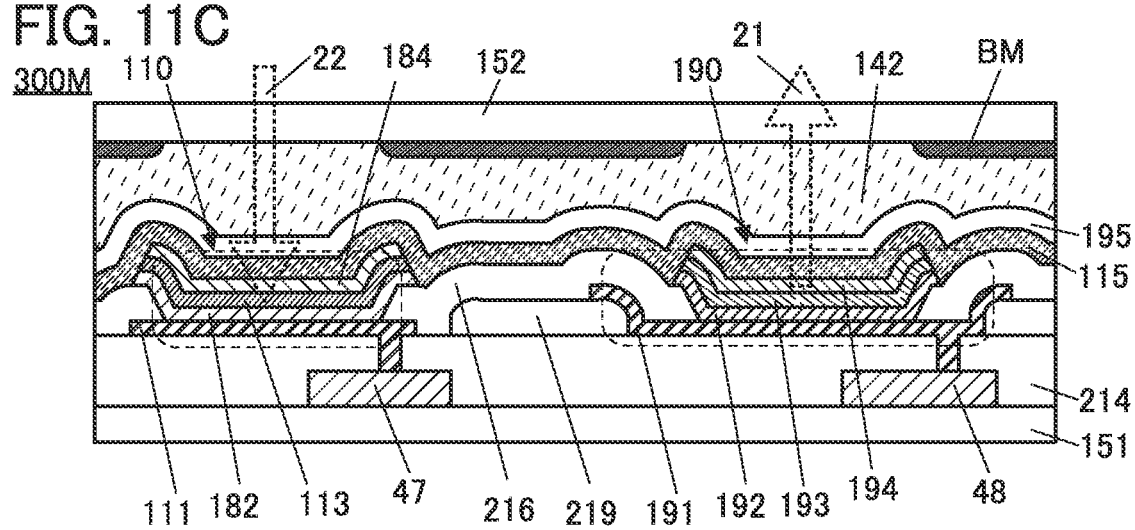

FIG. 11A is a cross-sectional view of a sensor device 300K, FIG. 11B is a cross-sectional view of a sensor device 300L, and FIG. 11C is a cross-sectional view of a sensor device 300M.

The sensor device 300K is different from the sensor device 300A in that the common layer 114 is not included and a buffer layer 184 and a buffer layer 194 are included. The buffer layer 184 and the buffer layer 194 may each have a single-layer structure or a stacked-layer structure.

In the sensor device 300K, the sensor element 110 includes the pixel electrode 111, the common layer 112, the active layer 113, the buffer layer 184, and the common electrode 115. In the sensor device 300K, the light-emitting element 190 includes the pixel electrode 191, the common layer 112, the light-emitting layer 193, the buffer layer 194, and the common electrode 115.

The sensor device 300L is different from the sensor device 300A in that the common layer 112 is not included and a buffer layer 182 and a buffer layer 192 are included. The buffer layer 182 and the buffer layer 192 may each have a single-layer structure or a stacked-layer structure.

In the sensor device 300L, the sensor element 110 includes the pixel electrode 111, the buffer layer 182, the active layer 113, the common layer 114, and the common electrode 115. In the sensor device 300L, the light-emitting element 190 includes the pixel electrode 191, the buffer layer 192, the light-emitting layer 193, the common layer 114, and the common electrode 115.

The sensor device 300M is different from the sensor device 300K or the sensor device 300L in that the common layer 112 and the common layer 114 are not included and the buffer layer 182, the buffer layer 184, the buffer layer 192, and the buffer layer 194 are included.

In the sensor device 300M, the sensor element 110 includes the pixel electrode 111, the buffer layer 182, the active layer 113, the buffer layer 184, and the common electrode 115. In the sensor device 300M, the light-emitting element 190 includes the pixel electrode 191, the buffer layer 192, the light-emitting layer 193, the buffer layer 194, and the common electrode 115.

Other layers as well as the active layer 113 and the light-emitting layer 193 can be formed separately when the sensor element 110 and the light-emitting element 190 are manufactured.

In the sensor device 300K, an example is shown in which the buffer layer 184 between the common electrode 115 and the active layer 113 and the buffer layer 194 between the common electrode 115 and the light-emitting layer 193 are formed separately. As the buffer layer 194, one or both of an electron-injection layer and an electron-transport layer can be formed, for example.

In the sensor device 300L, an example is shown in which the buffer layer 182 between the pixel electrode 111 and the active layer 113 and the buffer layer 192 between the pixel electrode 191 and the light-emitting layer 193 are formed separately. As the buffer layer 192, one or both of a hole-injection layer and a hole-transport layer can be formed, for example.

In the sensor device 300M, an example is shown in which in each of the sensor element 110 and the light-emitting element 190, a common layer is not provided between the pair of electrodes (the pixel electrode 111 or the pixel electrode 191 and the common electrode 115). The sensor element 110 and the light-emitting element 190 included in the sensor device 300M can be manufactured in the following manner: the pixel electrode 111 and the pixel electrode 191 are formed over the insulating layer 214 using the same material in the same step; the buffer layer 182, the active layer 113, and the buffer layer 184 are formed over the pixel electrode 111; the buffer layer 192, the light-emitting layer 193, and the buffer layer 194 are formed over the pixel electrode 191; and then, the common electrode 115 is formed to cover the pixel electrode 111, the buffer layer 182, the active layer 113, the buffer layer 184, the pixel electrode 191, the buffer layer 192, the light-emitting layer 193, and the buffer layer 194. Note that the manufacturing order of the stacked-layer structure of the buffer layer 182, the active layer 113, and the buffer layer 184 and the stacked-layer structure of the buffer layer 192, the light-emitting layer 193, and the buffer layer 194 is not particularly limited. For example, after the buffer layer 182, the active layer 113, and the buffer layer 184 are deposited, the buffer layer 192, the light-emitting layer 193, and the buffer layer 194 may be formed. In contrast, the buffer layer 192, the light-emitting layer 193, and the buffer layer 194 may be formed before the buffer layer 182, the active layer 113, and the buffer layer 184 are deposited. Alternatively, the buffer layer 182, the buffer layer 192, the active layer 113, and the light-emitting layer 193 may be deposited in that order, for example.

The detailed structure of the sensor device of one embodiment of the present invention is described below with reference to FIG. 12 to FIG. 15.

[Sensor Device 100A]

FIG. 12A is a cross-sectional view of the sensor device 100A.

The sensor device 100A has a structure in which the substrate 151 and the substrate 152 are bonded to each other. In FIG. 8A, the substrate 151 is denoted by a dashed line.

The sensor device 100A includes the light-emitting region 31a, the sensor region 41a, the circuit 42a, a wiring 165, and the like. FIG. 12A illustrates an example in which the FPC 172 is mounted on the sensor device 100A. Note that although not illustrated in FIG. 12A, the IC 173 illustrated in FIG. 8A is also mounted. Thus, the structure shown in FIG. 12A can also be regarded as a sensor module including the sensor device 100A, the IC, and the FPC.

The circuit 42a is a scan line driver circuit, for example.

The wiring 165 has a function of supplying a signal and power to the light-emitting region 31a, the sensor region 41a, and the circuit 42a. The signal and power are input to the wiring 165 from the outside through the FPC 172 or input to the wiring 165 from the IC 173 illustrated in FIG. 8A.

FIG. 12 illustrates examples of cross sections of the sensor device 100A illustrated in FIG. 8A when part of a region including the FPC 172, part of a region including the circuit 42a, part of a region including the sensor region 41a, part of a region including the light-emitting region 31a, part of a region including the region CL1, and part of a region including an end portion are cut.

The sensor device 100A illustrated in FIG. 12A includes a transistor 201, a transistor 205, a transistor 206, the light-emitting element 190, the sensor element 110, and the like between the substrate 151 and the substrate 152.

The substrate 152 and the insulating layer 214 are bonded to each other with the adhesive layer 142. A solid sealing structure, a hollow sealing structure, or the like can be employed to seal the light-emitting element 190 and the sensor element 110. In FIG. 12A, a hollow sealing structure is employed in which a space 143 surrounded by the substrate 152, the adhesive layer 142, and the insulating layer 214 is filled with an inert gas (e.g., nitrogen or argon). The adhesive layer 142 may be provided to overlap with the light-emitting element 190. The space 143 surrounded by the substrate 152, the adhesive layer 142, and the insulating layer 214 may be filled with a resin different from that of the adhesive layer 142.

The light-emitting element 190 has a stacked-layer structure in which the pixel electrode 191, the common layer 112, the light-emitting layer 193, the common layer 114, and the common electrode 115 are stacked in this order from the insulating layer 214 side. The partition wall 219 is positioned over the insulating layer 214, and the pixel electrode 191 includes the region 191a over and in contact with the insulating layer 214 and the partition wall 216. The pixel electrode 191 is connected to a conductive layer 222b included in the transistor 206 through an opening provided in the insulating layer 214. The transistor 206 has a function of controlling the driving of the light-emitting element 190. The end portion (the region 191a) of the pixel electrode 191 is covered with the partition wall 216. The pixel electrode 191 contains a material that reflects light and the common electrode 115 contains a material that transmits light.

The sensor element 110 has a stacked-layer structure in which the pixel electrode 111, the common layer 112, the active layer 113, the common layer 114, and the common electrode 115 are stacked in this order from the insulating layer 214 side. The pixel electrode 111 is electrically connected to the conductive layer 222b included in the transistor 205 through an opening provided in the insulating layer 214. End portions of the pixel electrode 111 are covered with the partition wall 216. The pixel electrode 111 contains a material that reflects light and the common electrode 115 contains a material that transmits light.

Light emitted from the light-emitting element 190 is emitted to the substrate 152 side. Light enters the sensor element 110 through the substrate 152 and the space 143. For the substrate 152, a material having a high transmitting property with respect to light is preferably used.

The pixel electrode 111 and the pixel electrode 191 can be formed using the same material in the same step. The common layer 112, the common layer 114, and the common electrode 115 are used in both the sensor element 110 and the light-emitting element 190. The sensor element 110 and the light-emitting element 190 can have common components except the active layer 113 and the light-emitting layer 193. Thus, the sensor element 110 can be incorporated into the sensor device 100A without a significant increase in the number of manufacturing steps.

The region 191a included in the pixel electrode 191 has a function of reflecting light emitted from the light-emitting element 190 and blocking diffusion light entering the sensor element. In addition, the region 191a has a function of reflecting light emitted from the light-emitting element 190 and collecting light in substantially the same direction as the direction of light emitted from the light-emitting element. Furthermore, the light-blocking layer BM is provided on the surface of the substrate 152 on the substrate 151 side. The light-blocking layer BM has openings at a position overlapping with the sensor element 110 and at a position overlapping with the light-emitting element 190. Providing the light-blocking layer BM can control a range where light is sensed by the sensor element 110. Furthermore, the light-blocking layer BM can inhibit direct entry of light into the sensor element 110 from the light-emitting element 190 without through an object. Thus, a sensor with less noise and high sensitivity can be achieved.

The transistor 201, the transistor 205, and the transistor 206 are formed over the substrate 151. These transistors can be manufactured using the same materials in the same process.

An insulating layer 211, an insulating layer 213, an insulating layer 215, and an insulating layer 214 are provided in this order over the substrate 151. Part of the insulating layer 211 functions as a gate insulating layer of each transistor. Part of the insulating layer 213 functions as a gate insulating layer of each transistor. The insulating layer 215 is provided to cover the transistors. The insulating layer 214 is provided to cover the transistors and has a function of a planarization layer. Note that the number of gate insulating layers and the number of insulating layers covering the transistors are not limited, and a single layer or two or more layers may be employed.

A material through which impurities such as water and hydrogen do not easily diffuse is preferably used for at least one of the insulating layers that cover the transistors. Thus, such an insulating layer can function as a barrier layer. Such a structure can effectively inhibit diffusion of impurities into the transistors from the outside, and the reliability of the sensor device can be increased.

An inorganic insulating film is preferably used as each of the insulating layer 211, the insulating layer 213, and the insulating layer 215. As the inorganic insulating film, an inorganic insulating film such as a silicon nitride film, a silicon oxynitride film, a silicon oxide film, a silicon nitride oxide film, an aluminum oxide film, or an aluminum nitride film can be used, for example. A hafnium oxide film, an yttrium oxide film, a zirconium oxide film, a gallium oxide film, a tantalum oxide film, a magnesium oxide film, a lanthanum oxide film, a cerium oxide film, a neodymium oxide film, or the like may also be used. A stack including two or more of the above insulating films may also be used.

Here, an organic insulating film often has a lower barrier property than an inorganic insulating film. Thus, the organic insulating film preferably has an opening in the vicinity of an end portion of the sensor device 100A. This can inhibit entry of impurities from the end portion of the sensor device 100A through the organic insulating film. Alternatively, the organic insulating film may be formed so that its end portion is positioned on the inner side compared to the end portion of the sensor device 100A, to prevent the organic insulating film from being exposed at the end portion of the sensor device 100A.

An organic insulating film is suitable for the insulating layer 214 functioning as a planarization layer. Examples of materials which can be used for the organic insulating film include an acrylic resin, a polyimide resin, an epoxy resin, a polyamide resin, a polyimide-amide resin, a siloxane resin, a benzocyclobutene-based resin, a phenol resin, and precursors of these resins.

In a region 228 illustrated in FIG. 12A, an opening is formed in the insulating layer 214. This can inhibit entry of impurities into the light-emitting region 31a and the sensor region 41a from the outside through the insulating layer 214 even when an organic insulating film is used as the insulating layer 214. Accordingly, the reliability of the sensor device 100A can be increased.

Each of the transistor 201, the transistor 205, and the transistor 206 includes a conductive layer 221 functioning as a gate, the insulating layer 211 functioning as the gate insulating layer, a conductive layer 222a and the conductive layer 222b functioning as a source and a drain, a semiconductor layer 231, the insulating layer 213 functioning as the gate insulating layer, and a conductive layer 223 functioning as a gate. Here, a plurality of layers obtained by processing the same conductive film are shown with the same hatching pattern. The insulating layer 211 is positioned between the conductive layer 221 and the semiconductor layer 231. The insulating layer 213 is positioned between the conductive layer 223 and the semiconductor layer 231.

There is no particular limitation on the structure of the transistor included in the sensor device of this embodiment. For example, a planar transistor, a staggered transistor, or an inverted staggered transistor can be used. A top-gate or a bottom-gate transistor structure may be used. Alternatively, gates may be provided above and below a semiconductor layer where a channel is formed.

The structure in which the semiconductor layer where a channel is formed is provided between the two gates is used for the transistor 201, the transistor 205, and the transistor 206. The two gates may be connected to each other and supplied with the same signal to operate the transistor. Alternatively, by applying a potential for controlling the threshold voltage to one of the two gates and a potential for driving to the other, the threshold voltage of the transistor may be controlled.

There is no particular limitation on the crystallinity of a semiconductor material used for the transistors, and an amorphous semiconductor or a semiconductor having crystallinity (a microcrystalline semiconductor, a polycrystalline semiconductor, a single-crystal semiconductor, or a semiconductor partly including crystal regions) may be used. A semiconductor having crystallinity is preferably used, in which case deterioration of the transistor characteristics can be suppressed.

It is preferable that the semiconductor layer of the transistor contain a metal oxide (also referred to as an oxide semiconductor). Alternatively, the semiconductor layer of the transistor may contain silicon. Examples of silicon include amorphous silicon and crystalline silicon (e.g., low-temperature polysilicon or single crystal silicon).

The semiconductor layer preferably contains indium, M (M is one or more kinds selected from gallium, aluminum, silicon, boron, yttrium, tin, copper, vanadium, beryllium, titanium, iron, nickel, germanium, zirconium, molybdenum, lanthanum, cerium, neodymium, hafnium, tantalum, tungsten, and magnesium), and zinc, for example. Specifically, M is preferably one or more kinds selected from aluminum, gallium, yttrium, and tin.

It is particularly preferable to use an oxide containing indium (In), gallium (Ga), and zinc (Zn) (also referred to as IGZO) for the semiconductor layer.

In the case where the semiconductor layer is an In-M-Zn oxide, a sputtering target used for depositing the In-M-Zn oxide preferably has the atomic proportion of In higher than or equal to the atomic proportion of M. Examples of the atomic ratio of the metal elements in such a sputtering target include In:M:Zn=1:1:1, In:M:Zn=1:1:1.2, In:M:Zn=2:1:3, In:M:Zn=3:1:2, In:M:Zn=4:2:3, In:M:Zn=4:2:4.1, In:M:Zn=5:1:6, In:M:Zn=5:1:7, In:M:Zn=5:1:8, In:M:Zn=6:1:6, and In:M:Zn=5:2:5.

A target containing a polycrystalline oxide is preferably used as the sputtering target, in which case the semiconductor layer having crystallinity is easily formed. Note that the atomic ratio in the formed semiconductor layer may vary from the above atomic ratio of metal elements in the sputtering target in a range of ±40%. For example, in the case where the composition of a sputtering target used for the semiconductor layer is In:Ga:Zn=4:2:4.1 [atomic ratio], the composition of the semiconductor layer to be formed is in some cases in the neighborhood of In:Ga:Zn=4:2:3 [atomic ratio].

Note that when the atomic ratio is described as In:Ga:Zn=4:2:3 or as being in the neighborhood thereof, the case is included where the atomic proportion of Ga is greater than or equal to 1 and less than or equal to 3 and the atomic proportion of Zn is greater than or equal to 2 and less than or equal to 4 with the atomic proportion of In being 4. When the atomic ratio is described as In:Ga:Zn=5:1:6 or as being in the neighborhood thereof, the case is included where the atomic proportion of Ga is greater than 0.1 and less than or equal to 2 and the atomic proportion of Zn is greater than or equal to 5 and less than or equal to 7 with the atomic proportion of In being 5. When the atomic ratio is described as In:Ga:Zn=1:1:1 or as being in the neighborhood thereof, the case is included where the atomic proportion of Ga is greater than 0.1 and less than or equal to 2 and the atomic proportion of Zn is greater than 0.1 and less than or equal to 2 with the atomic proportion of In being 1.

The transistor included in the circuit 42a, the transistor included in the sensor region 41a, and the transistor included in the light-emitting region 31a may have the same structure or different structures. A plurality of transistors included in the circuit 42a may have the same structure or two or more kinds of structures. Similarly, a plurality of transistors included in the light-emitting region 31a may have the same structure or two or more kinds of structures. Similarly, a plurality of transistors included in the sensor region 41a may have the same structure or two or more kinds of structures.

A connection portion 204 is provided in a region of the substrate 151 not overlapping with the substrate 152. In the connection portion 204, the wiring 165 is electrically connected to the FPC 172 through a conductive layer 166 and a connection layer 242. On a top surface of the connection portion 204, the conductive layer 166 obtained by processing the same conductive film as the pixel electrode 191 is exposed. Thus, the connection portion 204 and the FPC 172 can be electrically connected to each other through the connection layer 242. Note that the wiring 165 may be formed concurrently with the conductive layer 222 or the conductive layer 223.

Any of a variety of optical members can be placed on the outer side of the substrate 152. Examples of the optical members include a polarizing plate, a retardation plate, a light diffusion layer (a diffusion film or the like), an anti-reflective layer, and a light-condensing film. Furthermore, an antistatic film preventing the attachment of dust, a water repellent film suppressing the attachment of stain, a hard coat film suppressing generation of a scratch caused by the use, a shock absorption layer, or the like may be placed on the outer side of the substrate 152.

For each of the substrate 151 and the substrate 152, glass, quartz, ceramic, sapphire, a resin, or the like can be used. When a flexible material is used for the substrate 151 and the substrate 152, the flexibility of the sensor device can be increased.

As the adhesive layer, a variety of curable adhesives, e.g., a photocurable adhesive such as an ultraviolet curable adhesive, a reactive curable adhesive, a thermosetting adhesive, and an anaerobic adhesive can be used. Examples of these adhesives include an epoxy resin, an acrylic resin, a silicone resin, a phenol resin, a polyimide resin, an imide resin, a PVC (polyvinyl chloride) resin, a PVB (polyvinyl butyral) resin, and an EVA (ethylene vinyl acetate) resin. In particular, a material with low moisture permeability, such as an epoxy resin, is preferred. Alternatively, a two-component resin may be used. An adhesive sheet or the like may be used.

For the connection layer 242, an anisotropic conductive film, an anisotropic conductive paste, or the like can be used.

The light-emitting element 190 has a top-emission structure, a bottom-emission structure, a dual-emission structure, or the like. A conductive film that transmits light is used as the electrode through which light is extracted. A conductive film that reflects light is preferably used as the electrode through which no light is extracted.

The light-emitting element 190 includes at least the light-emitting layer 193. In addition to the light-emitting layer 193, the light-emitting element 190 may further include a layer containing a substance with a high hole-injection property, a substance with a high hole-transport property, a hole-blocking material, a substance with a high electron-transport property, a substance with a high electron-injection property, a substance with a bipolar property (a substance with a high electron- and hole-transport property), or the like. For example, the common layer 112 preferably includes one or both of a hole-injection layer and a hole-transport layer. For example, the common layer 114 preferably includes one or both of an electron-transport layer and an electron-injection layer.

Either a low molecular compound or a high molecular compound can be used for the common layer 112, the light-emitting layer 193, and the common layer 114, and an inorganic compound may also be contained. The layers included in the common layer 112, the light-emitting layer 193, and the common layer 114 can be formed by a method such as an evaporation method (including a vacuum evaporation method), a transfer method, a printing method, an inkjet method, or a coating method.

The light-emitting layer 193 may contain an inorganic compound such as quantum dots as a light-emitting material.

The active layer 113 of the sensor element 110 contains a semiconductor. Examples of the semiconductor include an inorganic semiconductor such as silicon and an organic semiconductor including an organic compound. This embodiment shows an example in which an organic semiconductor is used as the semiconductor contained in the active layer. The use of an organic semiconductor is preferable, in which case the light-emitting layer 193 of the light-emitting element 190 and the active layer 113 of the sensor element 110 can be formed by the same method (e.g., a vacuum evaporation method) and the same manufacturing apparatus can be used.

Examples of an n-type semiconductor material included in the active layer 113 are electron-accepting organic semiconductor materials such as fullerene (e.g., $C_{60}$ and $C_{70}$) and derivatives thereof. Examples of a p-type semiconductor material included in the active layer 113 are electron-donating organic semiconductor materials such as copper(II) phthalocyanine (CuPc) and tetraphenyldibenzoperiflanthene (DBP).

For example, the active layer 113 is preferably formed by co-evaporation of an n-type semiconductor and a p-type semiconductor.

Examples of materials that can be used for conductive layers of a variety of wirings and electrodes and the like included in the sensor device in addition to a gate, a source, and a drain of a transistor include metals such as aluminum, titanium, chromium, nickel, copper, yttrium, zirconium, molybdenum, silver, tantalum, and tungsten and an alloy containing such a metal as its main component. A film containing any of these materials can be used in a single layer or as a stacked-layer structure.

As a light-transmitting conductive material, a conductive oxide such as indium oxide, indium tin oxide, indium zinc oxide, zinc oxide, or zinc oxide containing gallium, or graphene can be used. Alternatively, a metal material such as gold, silver, platinum, magnesium, nickel, tungsten, chromium, molybdenum, iron, cobalt, copper, palladium, or titanium, or an alloy material containing any of these metal materials can be used. Alternatively, a nitride of the metal material (e.g., titanium nitride) or the like may be used. Note that in the case of using the metal material or the alloy material (or the nitride thereof), the thickness is preferably set small enough to be able to transmit light. A stacked film of any of the above materials can be used for the conductive layers. For example, a stacked film of indium tin oxide and an alloy of silver and magnesium, or the like is preferably used because the conductivity can be increased. They can also be used for the conductive layers such as the wirings and electrodes included in the sensor device, and conductive layers (a conductive layer serving as a pixel electrode or a common electrode) included in a display element.

As an insulating material that can be used for each insulating layer, for example, a resin such as an acrylic resin or an epoxy resin, and an inorganic insulating material such as silicon oxide, silicon oxynitride, silicon nitride oxide, silicon nitride, or aluminum oxide can be given.

In FIG. 12B, a connection portion 204a that is different from the connection portion in FIG. 12A is provided. In the connection portion 204a, the wiring 165 is electrically connected to the electrode 244 through the conductive layer 166 and a connection layer 243. On a top surface of the connection portion 204a, the conductive layer 166 obtained by processing the same conductive film as the pixel electrode 191 is exposed. Thus, the connection portion 204a and the electrode 244 can be electrically connected to each other through the connection layer 243. The electrode 244 preferably includes one or a plurality of copper, nickel, gold, silver, tin, and the like.

[Sensor Device 100B]

FIG. 13A is a cross-sectional view of a sensor device 100B.

The sensor device 100B is different from the sensor device 100A mainly in that the region CL2, the lens 149, and the protective layer 195 are included. The circuit 32e is arranged in the region CL2. The circuit 32e includes at least a transistor 203.

With the protective layer 195 covering the sensor element 110 and the light-emitting element 190, entry of impurities such as water into the sensor element 110 and the light-emitting element 190 can be inhibited, leading to an increase in the reliability of the sensor element 110 and the light-emitting element 190.

In the region 228 in the vicinity of an end portion of the sensor device 100B, the insulating layer 215 and the protective layer 195 are preferably in contact with each other through an opening in the insulating layer 214. In particular, an inorganic insulating film included in the insulating layer 215 and an inorganic insulating film included in the protective layer 195 are preferably in contact with each other. Thus, entry of impurities into the light-emitting region 31a from the outside through an organic insulating film can be inhibited. Accordingly, the reliability of the sensor device 100B can be increased.

FIG. 13B illustrates an example in which the protective layer 195 has a three-layer structure. In FIG. 13B, the protective layer 195 includes an inorganic insulating layer 195a over the common electrode 115, an organic insulating layer 195b over the inorganic insulating layer 195a, and an inorganic insulating layer 195c over the organic insulating layer 195b.

An end portion of the inorganic insulating layer 195a and an end portion of the inorganic insulating layer 195c extend beyond an end portion of the organic insulating layer 195b and are in contact with each other. The inorganic insulating layer 195a is in contact with the insulating layer 215 (inorganic insulating layer) through the opening in the insulating layer 214 (organic insulating layer). Accordingly, the sensor element 110 and the light-emitting element 190 can be surrounded by the insulating layer 215 and the protective layer 195, whereby the reliability of the sensor element 110 and the light-emitting element 190 can be increased.

As described above, the protective layer 195 may have a stacked-layer structure of an organic insulating film and an inorganic insulating film. In that case, an end portion of the inorganic insulating film preferably extends beyond an end portion of the organic insulating film.

The lens 149 is provided on a surface of the substrate 152 on the substrate 151 side. The lens 149 has a convex surface facing the substrate 151. It is preferable that the light-receiving region (sensor region) of the sensor element 110 overlap with the lens 149 and not overlap with the light-emitting layer 193. Thus, the sensitivity and accuracy of the sensor using the sensor element 110 can be increased.

The lens 149 preferably has a refractive index of greater than or equal to 1.3 and less than or equal to 2.5. The lens 149 can be formed using an inorganic material or an organic material. For example, a material containing a resin can be used for the lens 149. A material containing an oxide or a sulfide can be used for the lens 149.

Specifically, a resin containing chlorine, bromine, or iodine, a resin containing a heavy metal atom, a resin having an aromatic ring, a resin containing sulfur, and the like can be used for the lens 149. Alternatively, a material containing a resin and nanoparticles of a material having a higher refractive index than the resin can be used for the lens 149. Titanium oxide, zirconium oxide, or the like can be used for the nanoparticles.

In addition, cerium oxide, hafnium oxide, lanthanum oxide, magnesium oxide, niobium oxide, tantalum oxide, titanium oxide, yttrium oxide, zinc oxide, an oxide containing indium and tin, an oxide containing indium, gallium, and zinc, or the like can be used for the lens 149. Alternatively, zinc sulfide or the like can be used for the lens 149.

In the sensor device 100B, the protective layer 195 and the substrate 152 are bonded to each other with the adhesive layer 142. The adhesive layer 142 is provided to overlap with the sensor element 110 and the light-emitting element 190, and the sensor device 100B employs a solid sealing structure.

[Sensor Device 100C]

FIG. 14A is a cross-sectional view of a sensor device 100C.

The sensor device 100C is different from the sensor device 100B in the structure of a transistor. In addition, the sensor device 100C includes the region CL3. The wiring 165 is arranged in the region CL3. Note that the sensor device 100C shows an example in which the wiring 165 is formed concurrently with the conductive layer 222.

The sensor device 100C includes a transistor 208, a transistor 209, and a transistor 210 over the substrate 151.

Each of the transistor 208, the transistor 209, and the transistor 210 includes the conductive layer 221 functioning as a gate, the insulating layer 211 functioning as a gate insulating layer, a semiconductor layer including a channel formation region 231i and a pair of low-resistance regions 231n, the conductive layer 222a connected to one of the pair of low-resistance regions 231n, the conductive layer 222b connected to the other of the pair of low-resistance regions 231n, the insulating layer 213 functioning as a gate insulating layer, the conductive layer 223 functioning as a gate, and the insulating layer 215 covering the conductive layer 223. The insulating layer 211 is positioned between the conductive layer 221 and the channel formation region 231i. The insulating layer 213 is positioned between the conductive layer 223 and the channel formation region 231i.

The conductive layer 222a and the conductive layer 222b are connected to the respective low-resistance regions 231n through openings provided in the insulating layer 213 and the insulating layer 215. One of the conductive layer 222a and the conductive layer 222b functions as a source and the other functions as a drain.

The pixel electrode 191 of the light-emitting element 190 is electrically connected to one of the pair of low-resistance regions 231n of the transistor 208 through the conductive layer 222b.

The pixel electrode 111 of the sensor element 110 is electrically connected to the other of the pair of low-resistance regions 231n of the transistor 209 through the conductive layer 222b.

FIG. 14A shows an example in which the insulating layer 213 covers a top surface and a side surface of the semiconductor layer. Meanwhile, in FIG. 14B, the insulating layer 225 overlaps with the channel formation region 231i of the semiconductor layer 231 and does not overlap with the low-resistance regions 231n. The structure shown in FIG. 14B can be manufactured by processing the insulating layer 225 using the conductive layer 223 as a mask, for example. The transistor 208 to the transistor 210 can be replaced with a transistor 202 illustrated in FIG. 14B. In FIG. 14B, the insulating layer 215 is provided to cover the insulating layer 225 and the conductive layer 223, and the conductive layer 222a and the conductive layer 222b are connected to the low-resistance regions 231n through openings in the insulating layer 215. Furthermore, an insulating layer 218 covering the transistor may be provided.

[Sensor Device 100D]

Figure 15:
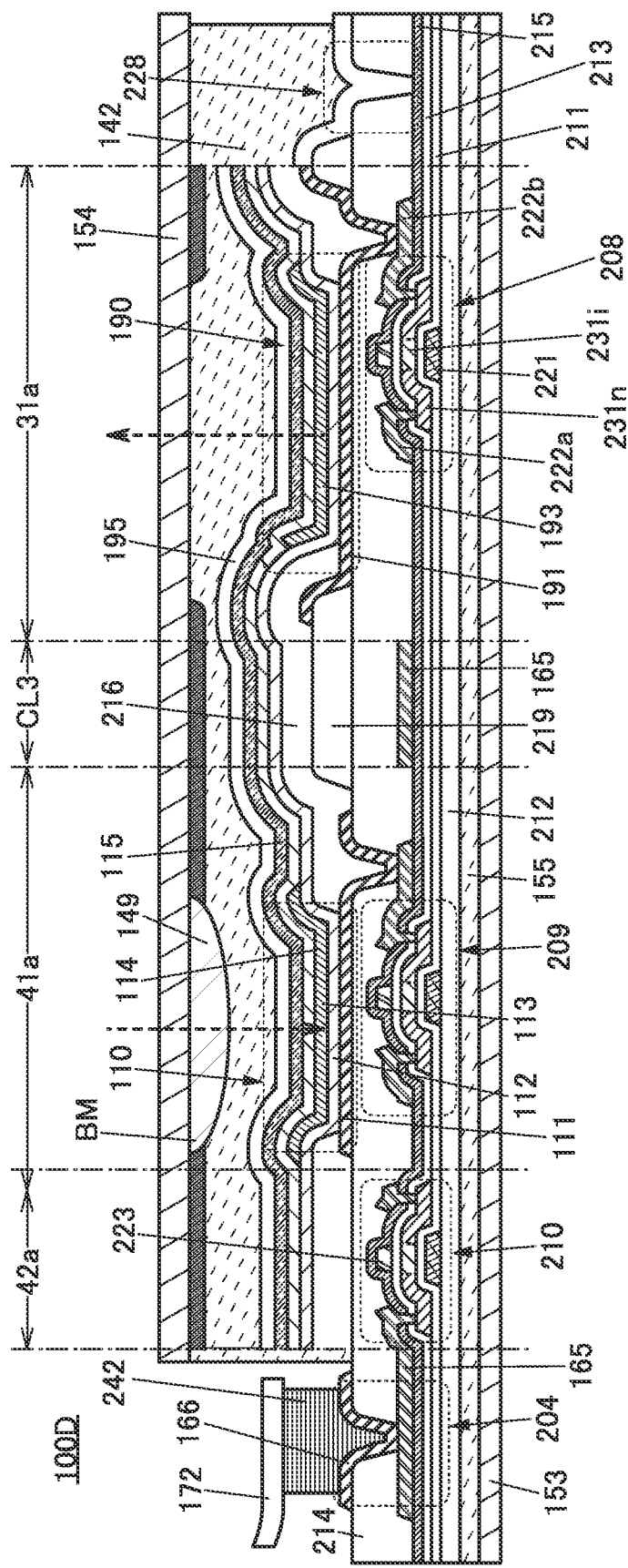
FIG. 15 is a cross-sectional view illustrating an example of a sensor device.

FIG. 15 is a cross-sectional view of a sensor device 100D.

The sensor device 100D is different from the sensor device 100C mainly in that the substrate 151 and the substrate 152 are not included and the substrate 153, the substrate 154, the adhesive layer 155, the insulating layer 212, and the lens 149 are included.

The substrate 153 and the insulating layer 212 are bonded to each other with the adhesive layer 155. The substrate 154 and the protective layer 195 are bonded to each other with the adhesive layer 142.

The sensor device 100D is formed in such a manner that the insulating layer 212, the transistor 208, the transistor 209, the sensor element 110, the light-emitting element 190, and the like that are formed over a formation substrate are transferred onto the substrate 153. The substrate 153 and the substrate 154 are preferably flexible. Accordingly, the flexibility of the sensor device 100D can be increased.

The inorganic insulating film that can be used as the insulating layer 211, the insulating layer 213, and the insulating layer 215 can be used as the insulating layer 212.

The sensor device 100C is an example of not including the lens 149 and the sensor device 100D is an example of including the lens 149. The lens 149 can be provided as appropriate in accordance with the usage of the sensor, or the like.

As described above, the sensor device of this embodiment includes the light-emitting element in the light-emitting region and the sensor element in the sensor region, the light-emitting region has a function of emitting light, and the sensor region has a function of sensing light in a wavelength range including a peak wavelength of light emitted from the light-emitting region. Accordingly, the size and weight of an electronic device can be reduced as compared to the case where a sensor is provided outside a light-emitting region or outside a sensor device. Moreover, an electronic device having more functions can be obtained by a combination with a sensor provided outside the light-emitting region or outside the sensor device.

The sensor element can have a structure in which at least one layer other than an active layer is shared with the light-emitting element. Furthermore, the sensor element can have a structure in which all layers other than an active layer are shared with the light-emitting element. For example, the light-emitting element and the sensor element can be formed over the same substrate by adding a step of depositing an active layer to the manufacturing process of the light-emitting element. In the sensor element and the light-emitting element, their pixel electrodes can be formed using the same material in the same step, and their common electrodes can be formed using the same material in the same step. When a circuit electrically connected to the sensor element and a circuit electrically connected to the light-emitting element are manufactured using the same material in the same process, the manufacturing process of the sensor device can be simplified. In this manner, a highly convenient sensor device incorporating a sensor element can be manufactured without a complicated process.

Moreover, in the sensor device of this embodiment, the pixel electrode included in the light-emitting element has a light-blocking function and a light-collecting function, and a coloring layer is provided between the sensor element and the light-emitting element. The coloring layer may also serve as a partition wall that electrically isolates the sensor element from the light-emitting element. The coloring layer can absorb diffusion light in the sensor device and thus can increase the sensitivity of the sensor using the sensor element.

At least part of the structure examples, the drawings corresponding thereto, and the like exemplified in this embodiment can be implemented in combination with the other structure examples, the other drawings, and the like as appropriate.

At least part of this embodiment can be implemented in combination with the other embodiments described in this specification as appropriate.

Embodiment 3

In this embodiment, examples of electronic devices in which the sensor device of one embodiment of the present invention can be used will be described.

Figure 16A:
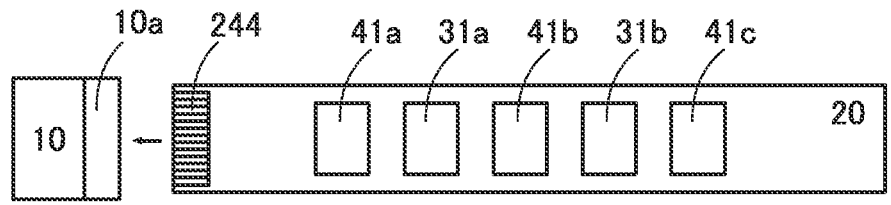
FIG. 16A to FIG. 16D are diagrams illustrating electronic devices.

FIG. 16A illustrates the electronic device 500 described in Embodiment 1 or Embodiment 2. The electronic device 500 includes the semiconductor device 10 and the sensor device 20. The semiconductor device 10 includes a processor, a memory, a battery, an image processing circuit, a communication module, or the like. Note that the semiconductor device 10 further includes a socket portion 10a and has a structure in which the sensor device 20 having flexibility is inserted into the socket portion 10a.

The sensor device 20 includes the light-emitting regions (31a, 31b), the sensor regions (41a, 41b, 41c), and a terminal including a plurality of electrodes 244. The light-emitting regions (31a, 31b) can each emit light with a different peak wavelength. The sensor regions (41a, 41b, 41c) include peak wavelengths of light emitted from the light-emitting regions in their sensing ranges; thus, different peak wavelengths can be sensed at the same time.

Figure 16B:
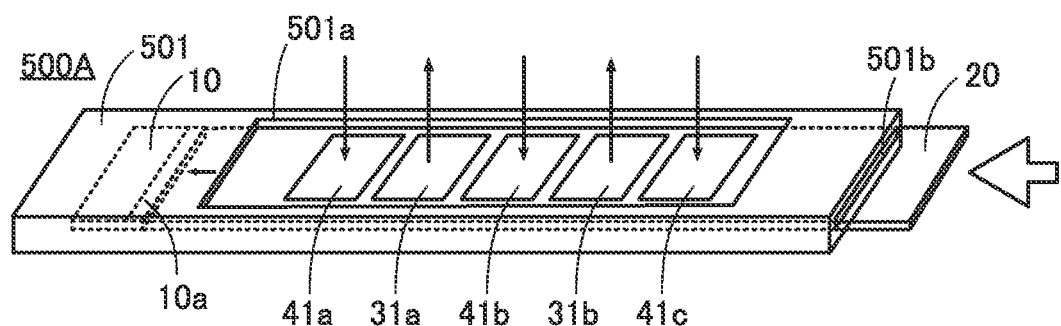

FIG. 16B illustrates an electronic device 500A. The electronic device 500A includes a housing 501. The housing 501 includes an opening portion 501a and an insertion portion 501b. The semiconductor device 10 is preferably stored in the housing 501. The sensor device 20 is inserted from the insertion portion 501b and electrically connected to the semiconductor device 10 through the socket portion 10a inside the housing 501. The light-emitting regions (31a, 31b) and the sensor regions (41a, 41b, 41c) are preferably positioned in the opening portion 501a.

Figure 16C:
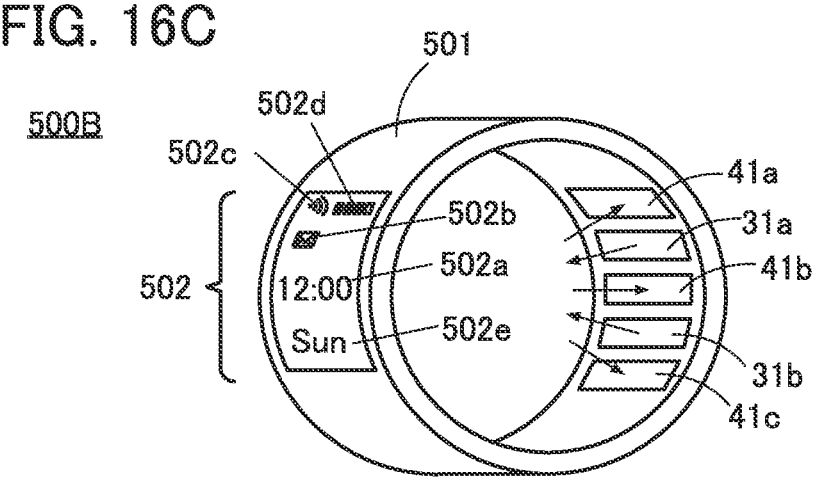

FIG. 16C illustrates an electronic device 500B. The electronic device 500B is a portable terminal incorporating the electronic device 500. The portable terminal includes a display portion 502, and a watch 502a, sending and receiving emails 502b, a communication function 502c, battery control 502d, a calendar 502e, a calling function, and the like can be operated with the display portion 502. The display portion 502 is arranged on the outer surface of the electronic device 500B, and the sensor device 20 is arranged on the inner surface of the electronic device 500B.

Figure 16D:
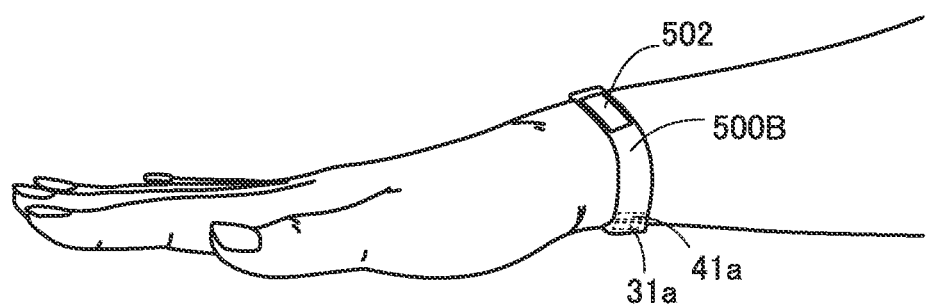

FIG. 16D illustrates, as an example, the electronic device 500B put on a wrist. The sensor device 20 is arranged to face inside; thus, the sensor device functions as a physiological monitor. For example, the blood sugar level can be monitored by sensing the amount of glucose in the blood. The sensed amount of glucose is stored in a memory of the portable terminal as data, and a change in the amount of glucose in the blood through a day can be monitored. By monitoring the change in the amount of glucose in the blood, the electronic device 500B can inform the user of administration timing of insulin a diabetic administers by vibration, display, lighting, or the like. The data can be transmitted to a server or the like by the communication function 502c.

Figure 17A:
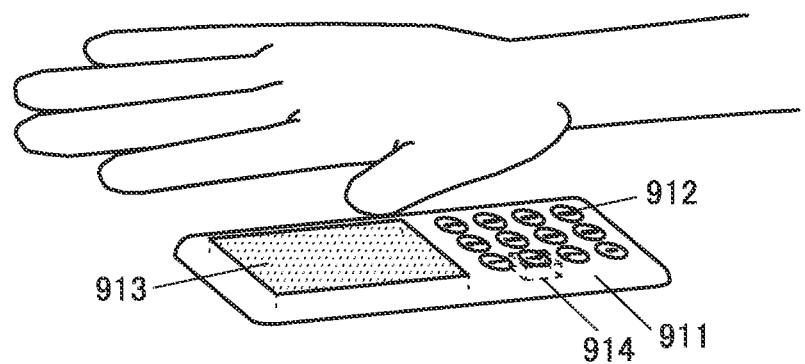
FIG. 17A to FIG. 17C are diagrams illustrating electronic devices.

FIG. 17A illustrates a biometric authentication device including a thin housing 911, an operation button 912, a sensor device 913, and the like. By holding the hand or finger over the sensor device 913 or touching the sensor device 913 with the hand or finger, the shape of the vein can be identified. A wireless communication unit 914 transmits the obtained data to a server, and the data is compared with a database; thus, personal identification is possible. Furthermore, a security code or the like can be input with the operation button. With the sensor device 913 of one embodiment of the present invention, a thin authentication device including a light-emitting region and a sensor region can be formed. The small thickness facilitates the incorporation into various devices. In addition, the portability is also increased.

Figure 17B:
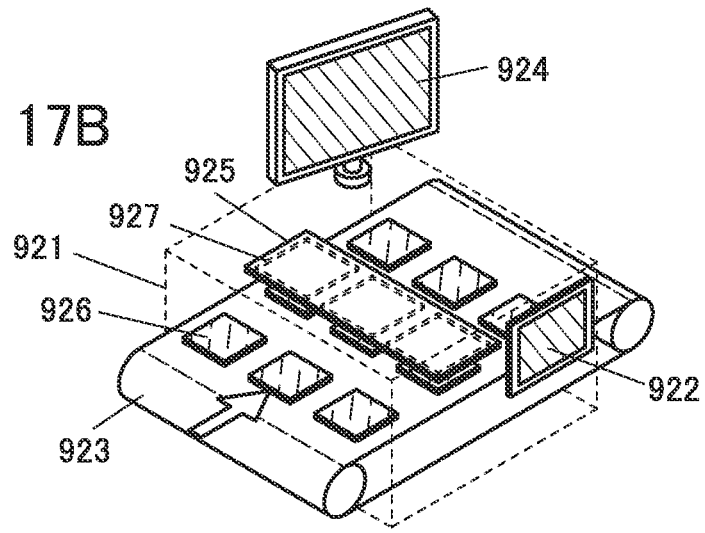

FIG. 17B illustrates a non-destructive testing device including a housing 921, an operation panel 922, a transfer mechanism 923, a monitor 924, a sensing unit 925, and the like. The sensing unit 925 includes a sensor device. Testing target members 926 are transported to the position directly under the sensing unit 925 by the transfer mechanism 923. A sensing device 927 of one embodiment of the present invention provided in the sensing unit 925 performs image capturing on the testing target members 926, and the captured image is displayed on the monitor 924. After that, the testing target members 926 are transported to an exit of the housing 921 and a defective member is separately collected. Image capturing using infrared light enables non-destructive and high-speed sensing of defective elements inside the non-testing target members, such as defects and foreign substances. In the sensor device 927 of one embodiment of the present invention, a light-emitting region and a sensor region can be formed at the same time, so that the sensing unit 925 can be formed at low costs.

Figure 17C:
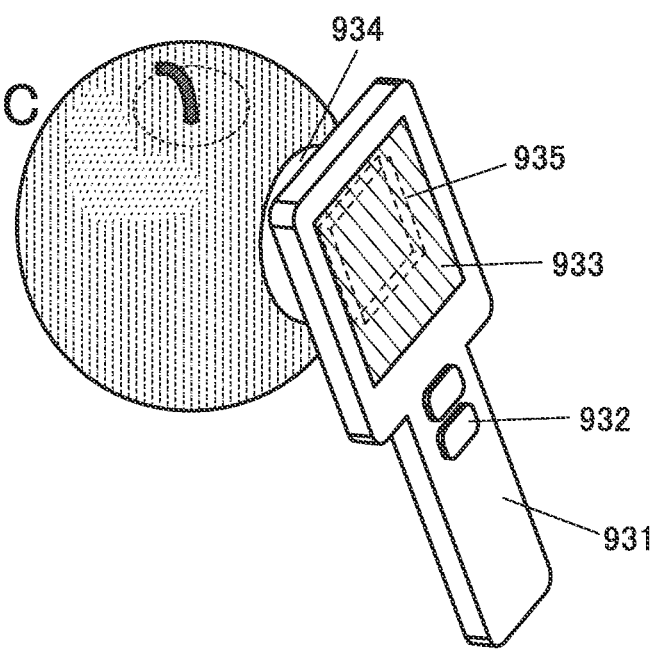

FIG. 17C illustrates a food screening device including a housing 931, an operation button 932, a display portion 933, a light-blocking hood 934, and the like. The light-blocking hood 934 provided in the periphery of the light-receiving portion is brought into intimate contact with a food of the inspection target, such as a fruit, and image capturing is performed; thus, a foreign substance mixed into the food, a bug, a cavity or spoilage inside the food, and the like can be detected. Furthermore, the sugar content, moisture content, or the like of foods can also be determined from the intensity of the detected infrared light. The food screening device can sort out defectives, classify foods according to the grade, and determine the harvest time. A sensor device 935 of one embodiment of the present invention provided in the light-receiving portion includes a light-emitting region and a sensor region; therefore, a thin, lightweight, and highly portable food screening device can be formed at low costs. Note that the structure illustrated in FIG. 17B may be used for the food screening device. Alternatively, the structure illustrated in FIG. 17C may be used for the non-destructive testing device.

This embodiment can be combined with any of the other embodiments as appropriate.

REFERENCE NUMERALS

G1: wiring, G1a: wiring, G2: wiring, G2a: wiring, G3: wiring, S1: wiring, S2: wiring, SR1: wiring, SR2: wiring, 10: semiconductor device, 10a: socket portion, 11: processor, 12: memory, 13: battery, 14: communication device, 15: image processing circuit, 20: sensor device, 20a: sensor device, 21: emitted light, 22: light, 23a: light, 23b: reflected light, 23c: light, 23d: reflected light, 30: region, 31: light-emitting region, 31a: light-emitting region, 31b: light-emitting region, 32: circuit, 32a: shift register, 32b: selector circuit, 32e: circuit, 33: circuit, 35: pixel, 40: region, 41: sensor region, 41a: sensor region, 41b: sensor region, 41c: sensor region, 42: circuit, 42a: circuit, 42b: circuit, 43: circuit, 44: circuit, 45: pixel, 46: circuit, 46a: circuit, 47: transistor, 48: transistor, 51: transistor, 52: transistor, 53: transistor, 54: transistor, 55: capacitor, 56: light-emitting element, 61: wiring, 62: wiring, 63: wiring, 64: wiring, 65: wiring, 66: wiring, 67: wiring, 68: wiring, 71: transistor, 72: transistor, 73: transistor, 74: transistor, 75: transistor, 76: capacitor, 77: capacitor, 78: sensor element, 81: transistor, 82: transistor, 83: terminal, 84: terminal, 90: server, 91: network, 100A: sensor device, 100B: sensor device, 100C: sensor device, 100D: sensor device, 110: sensor element, 111: pixel electrode, 112: common layer, 113: active layer, 114: common layer, 115: common electrode, 142: adhesive layer, 143: space, 146: lens array, 149: lens, 151: substrate, 152: substrate, 153: substrate, 154: substrate, 155: adhesive layer, 165: wiring, 166: conductive layer, 172: FPC, 173: IC, 182: buffer layer, 184: buffer layer, 190: light-emitting element, 191: pixel electrode, 191a: region, 192: buffer layer, 193: light-emitting layer, 194: buffer layer, 195: protective layer, 195a: inorganic insulating, 195b: organic insulating layer, 195c: inorganic insulating layer, 201: transistor, 203: transistor, 204: connection portion, 204a: connection portion, 205: transistor, 206: transistor, 208: transistor, 209: transistor, 210: transistor, 211: insulating layer, 212: insulating layer, 213: insulating layer, 214: insulating layer, 215: insulating layer, 216: partition wall, 217: partition wall, 218: insulating layer, 219: partition wall, 219a: partition wall, 221: conductive layer, 222: conductive layer, 222a: conductive layer, 222b: conductive layer, 223: conductive layer, 225: insulating layer, 228: region, 231: semiconductor layer, 231i: channel formation region, 231n: low-resistance region, 242: connection layer, 243: connection layer, 244: electrode, 300A: sensor device, 300B: sensor device, 300C: sensor device, 300K: sensor device, 300L: sensor device, 300M: sensor device.

The invention claimed is:

1. A semiconductor device comprising:
    a sensor device;
    a processor; and
    a communication device,
    wherein the sensor device comprises a first pixel and a second pixel formed over a substrate,
    the first pixel comprising:
        a light-emitting element; and
        a first transistor,
    the second pixel comprising:
        a sensor element having a photoelectric conversion function; and
        a second transistor,
    wherein a first insulating layer is over the first transistor,
    wherein a second insulating layer is over the first insulating layer,
    wherein light emitted from the light-emitting element has a peak wavelength,
    wherein a range of wavelength sensed by the sensor element comprises the peak wavelength,
    wherein the first transistor and the second transistor comprise the same element in their semiconductor layers,
    wherein a pixel electrode included in the light-emitting element is configured to be electrically connected to the first transistor and to block diffusion light to the sensor element,
    wherein the pixel electrode included in the light-emitting element comprises a region in contact with a top surface of the first insulating layer, and
    wherein an end portion of the pixel electrode included in the light-emitting element comprises a region in contact with a top surface of the second insulating layer.

2. The semiconductor device according to claim 1, wherein the second insulating layer comprises a region between the first pixel and the second pixel.

3. The semiconductor device according to claim 1,
    wherein light sensed by the sensor element is subjected to arithmetic operation in the processor, and
    wherein the communication device transmits a result of the arithmetic operation.

4. The semiconductor device according to claim 1, wherein the sensor device is configured to sense the amount of glucose in blood.

5. A sensor device comprising a first pixel and a second pixel formed over a substrate,
    the first pixel comprising:

a light-emitting element; and
a first transistor,
the second pixel comprising:
a sensor element having a photoelectric conversion function; and
a second transistor,
wherein a first insulating layer is over the first transistor,
wherein a second insulating layer is over the first insulating layer,
wherein light emitted from the light-emitting element has a peak wavelength,
wherein a range of wavelength sensed by the sensor element comprises the peak wavelength,
wherein the first transistor and the second transistor comprise the same element in their semiconductor layers,
wherein a pixel electrode included in the light-emitting element is configured to be electrically connected to the first transistor and to block diffusion light to the sensor element,
wherein the pixel electrode included in the light-emitting element comprises a region in contact with a top surface of the first insulating layer, and
wherein an end portion of the pixel electrode included in the light-emitting element comprises a region in contact with a top surface of the second insulating layer.

6. The sensor device according to claim 5, wherein the substrate is flexible.

7. The sensor device according to claim 5, wherein the peak wavelength is greater than or equal to 700 nm and less than or equal to 9000 nm.

8. The sensor device according to claim 5,
wherein the light-emitting element comprises a first organic compound and a common layer, and
wherein the sensor element comprises a second organic compound and the common layer.

9. The sensor device according to claim 5, wherein a region comprising no conductive layer is provided between the first pixel and the second pixel.

10. The sensor device according to claim 5, wherein the first transistor and the second transistor each comprise a metal oxide in the semiconductor layer.

11. The sensor device according to claim 10, wherein the first transistor or the second transistor comprises a back gate.

12. The sensor device according to claim 5, wherein the second insulating layer comprises a region between the first pixel and the second pixel.

13. The sensor device according to claim 5, wherein the sensor device is configured to sense the amount of glucose in blood.

* * * * *